United States Patent [19]
Smith et al.

[11] Patent Number: 5,846,529
[45] Date of Patent: Dec. 8, 1998

[54] INFUSION OF NEUTROPHIL PRECURSORS FOR TREATMENT OF NEUTROPENIA

[75] Inventors: Stephen L. Smith, Arlington Heights; Xiaoying Qiao, Waukegan, both of Ill.; Susan M. Maciukas, El Cerrito, Calif.; Maureen F. Loudovaris, Grayslake, Ill.; James G. Bender, Lindenhurst, Ill.; Dennis E. Van Epps, Cary, Ill.

[73] Assignee: Nexell Therapeutics, Inc., Irvine, Calif.

[21] Appl. No.: 376,945

[22] Filed: Jan. 20, 1995

Related U.S. Application Data

[63] Continuation-in-part of Ser. No. 295,378, Aug. 23, 1994, abandoned, which is a continuation-in-part of Ser. No. 110,277, Aug. 23, 1993, abandoned.

[51] Int. Cl.$^6$ ........................................................ C12N 5/00
[52] U.S. Cl. ........................ 424/93.7; 424/93.71; 435/325
[58] Field of Search ............................... 424/93.7, 93.71; 435/325

[56] References Cited

U.S. PATENT DOCUMENTS

| | | |
|---|---|---|
| 4,786,599 | 11/1988 | Chessebeuf et al. . |
| 4,816,401 | 3/1989 | Taupier et al. . |
| 5,004,681 | 4/1991 | Boyse et al. . |
| 5,045,467 | 9/1991 | Bertheussen . |
| 5,063,157 | 11/1991 | Stockinger . |
| 5,135,866 | 8/1992 | Herfetz et al. . |
| 5,155,036 | 10/1992 | Hagiwara et al. . |
| 5,199,942 | 4/1993 | Gillis . |
| 5,232,848 | 8/1993 | Wolfe et al. . |
| 5,541,103 | 7/1996 | Kanz et al. . |

FOREIGN PATENT DOCUMENTS

| | | |
|---|---|---|
| WO 90/15877 | 12/1990 | WIPO . |
| WO 92/06178 | 4/1992 | WIPO . |
| WO 92/11355 | 7/1992 | WIPO . |
| WO 92/18615 | 10/1992 | WIPO . |
| WO 93/18136 | 9/1993 | WIPO . |
| WO 93/18648 | 9/1993 | WIPO . |

OTHER PUBLICATIONS

ATCC "Hybridomas" in: *Catalogue of Cell Lines & Hybridomas*, 7th ed., pp. 320, 348, 374, 421 (1992).
ATCC Catalogue of Cell Lines and Hybridomas, 6th ed., pp. 342–355 (1988).
Bjare, *Pharma. Ther.* 53:355–374 (1992).
Bruno et al., "Effect of Interleukin 6 and Interleukin 1 on in vitro Human Megakaryocytopoiesis: Its Interaction with Other Cytokines," *Exp. Hematol.* 17:1038–1043 (1989).
Burrow et al., *Proc. Natl. Acad. Sci.* 90:6066–6070 (1993).
Da et al., *Brit. J. Haematol.* 78:42–47 (1991).
Dexter et al., *J Cell Physiol* 91:335 (1977).
Douay et al., *Exp. Hematol.* 14:358–365 (1986).
Drouet et al., *J. of Haemotol.* 73 (2):143–147 (1989).
Egeland et al.,"Myeloid Differentiation of Purified CD34$^+$ Cells After Stimulation With Recombinant Human Granulocyte–Monocyte Colony–Stimulating Factor (CSF), Granulocyte–CSF, Monocyte–CSF, and Interleukin–3", *Blood*, 78 (12):3192–3199 (1991).
Hardwick et al., *J. Hematother.* 1:379–386 (1992).
Hayrock, *Blood* 80 (6), pp. 1406–1412 (1992).
Jakoby et al. (eds.), *Meth. in Enzymology* LVIII (Cell Culture): 44–109 (1979).
Jandl, *Blood, Textbook of Hematology* 441–480 (1987).
Koike et al., "Interleukin–6 Enhances Murine Megakaryocytopoiesis in Serum–Free Culture," *Blood* 75 (12):2286–2291 (1990).
Koller et al., *Bio/Tech.* 11:358–363.
Kubota et al., "Murine Granulocyte/Macrophage and Megacaryocyte Colony Formation in Serum–Free Cultures," *Biol. Abs.* 82 (1986).
Lansdorp et al., *J. Exp. Med.* 175:1501–1509 (1991).
Long, *Stem Cells* 11:33–44 (1993).
Marmont et al., *Atlas of Blood Cells, Function and Pathology* in "Neutrophils" pp. 159–190.
Merchav et al., *Intl. J. Cell Cloning* 2:356–367 (1984).
Metcalf et al., *Proc. Natl. Acad. Sci.* 72:1744 (1975).
Nakef et al., *Ser Heamat* 8:4 (1975).
Okano et al. *ACTA Haemotol.* (*JPN*) 53:1213–1221 (1990).
Paulus, "Platelet kinetics" in: Williams et al. (eds.) *Hematol.* 1251–1260 (1990).
Ponting et al., *Growth Factors* 4:165–713 (1991).
Smith et al., *Exp. Hematol.* 21:870–877 (1993).
Somerville et al., "Future Directions in Transplantation: Xenotransplantation," *Kidney Intl.* 44 (suppl 42): S–112–S–121 (1993).
Spitzer et al., *Blood* 55:317–323.
Spooncer et al., *Differentiation* 31:111–118 (1986).
Teramura et al., "Clonal Growth of Human Megakaryocyte Progenitors in Serum–Free Cultures: Effect of Recombinant Human Interleukin 3" *Exp. Hematol.* 16:843–848 (1988).
Vincent et al., *Exp. Hematol.* 20 (1):17–23 (1992).
Warren et al., "The Role of Interleukin 6 and Interleukin 1 in Megakaryocyte Development," *Exp. Hematol.* 17 (11), pp. 1095–1099 (1989).
Wu et al., *Pathol.* 22:145–148 (1990).

*Primary Examiner*—Leon B. Lankford, Jr.
*Attorney, Agent, or Firm*—Campbell & Flores L.L.P.

[57] ABSTRACT

The invention provides a method of treating a patient having a reduced population of neutrophils following a myeloablative cancer treatment such as high dose chemotherapy. Following myeloablative therapy, a cell composition of at least 25% neutrophil precursors, i.e. promyelocytes, myelocytes, and metamyelocytes, is administered to the patient. Thereafter, the neutrophil precursors differentiate rapidly in vivo to replenish the supply of mature neutrophils for fighting infection. The method is used to reduce the neutropenic window between the time of myeloablative therapy and the time required for infused stem cells to proliferate and differentiate into mature neutrophils.

14 Claims, 13 Drawing Sheets

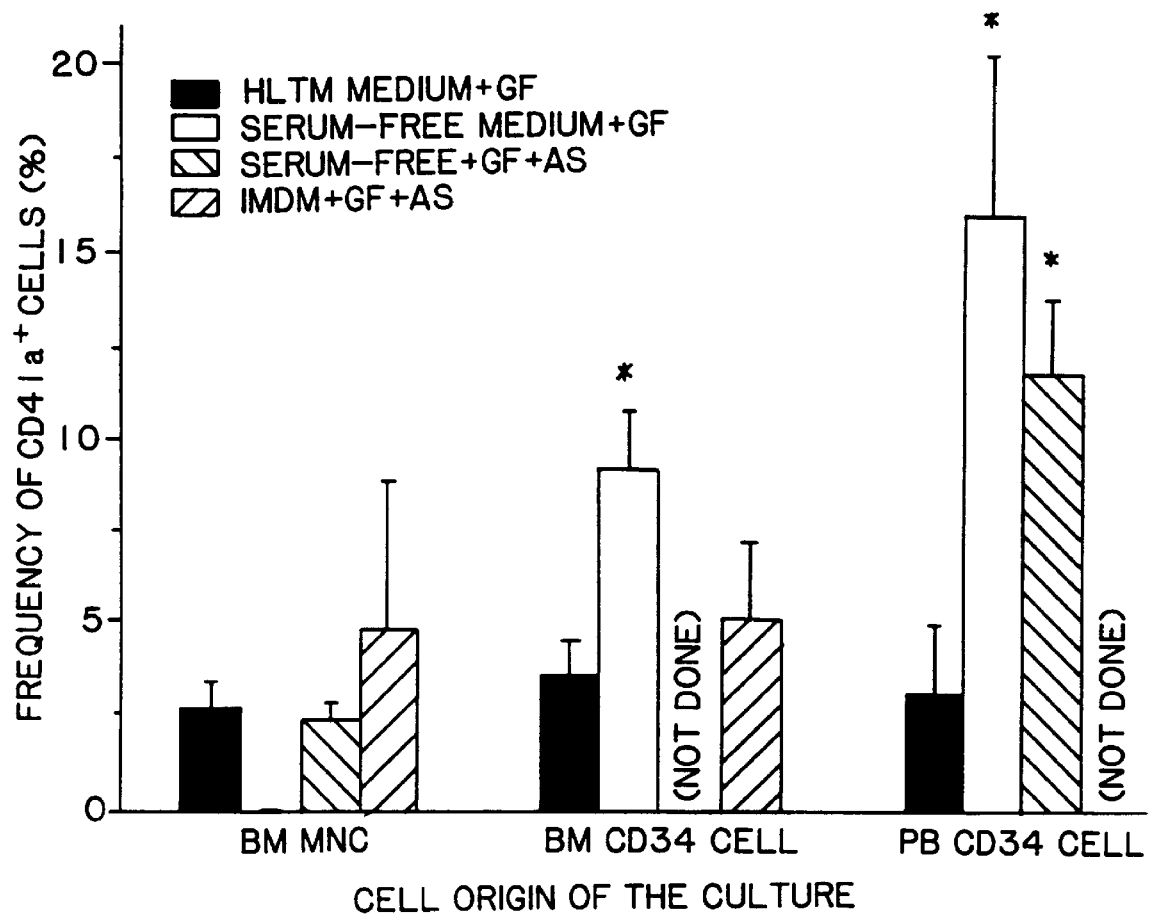

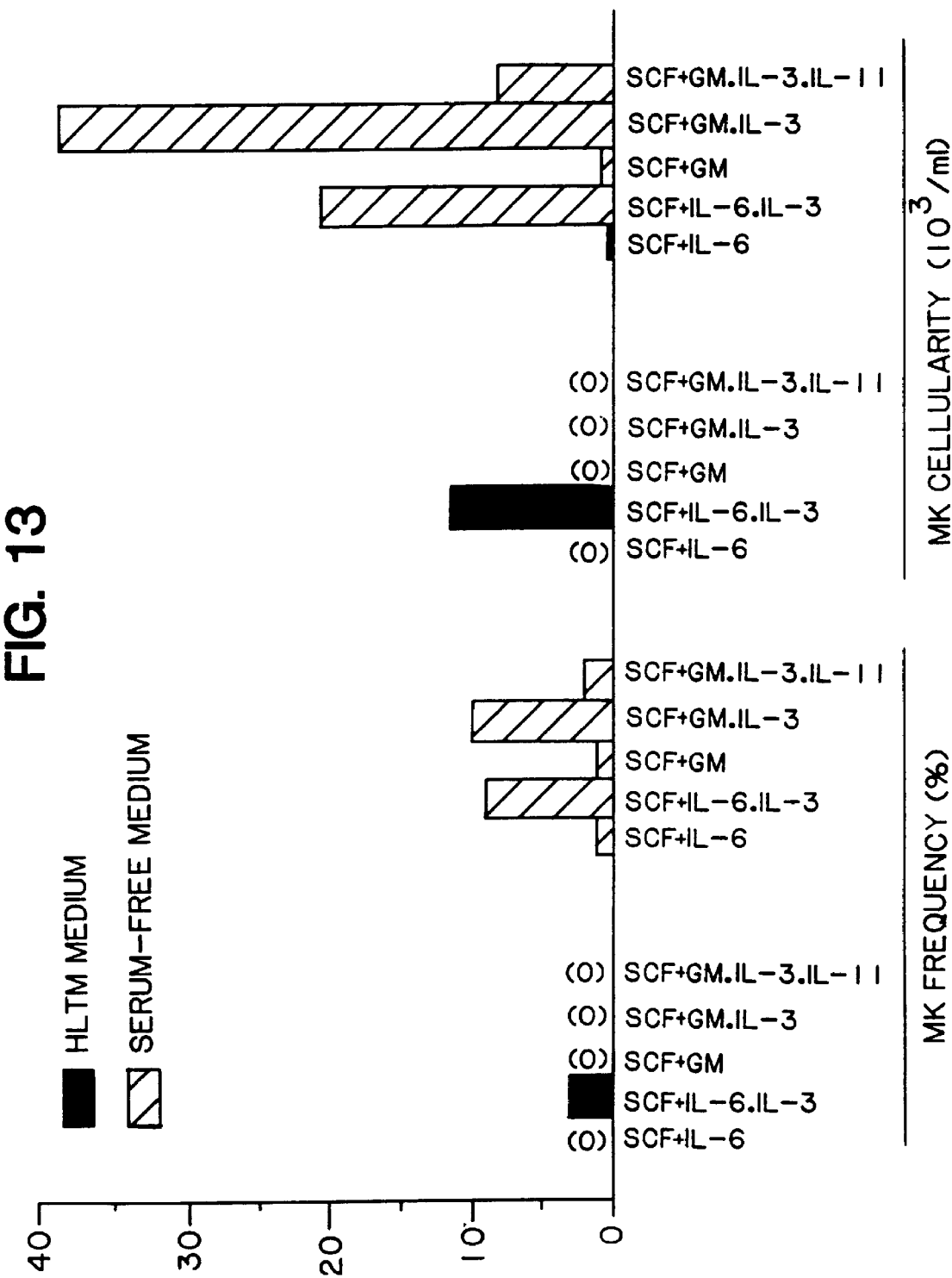

INFUSION OF NEUTROPHIL PRECURSORS FOR TREATMENT OF NEUTROPENIA

CROSS-REFERENCE TO RELATED APPLICATIONS

This application is a continuation-in-part of U.S. Ser. No. 08/295,378, filed Aug. 23, 1994, which in turn is a continuation-in-part of U.S. Ser. No. 08/110,277, filed Aug. 23, 1993, the contents of both of which are hereby incorporated by reference into the present disclosure.

TECHNICAL FIELD

The invention relates generally to transfusion treatments for neutropenia. More specifically, the invention relates to infusion of cell suspensions enriched for neutrophil precursors.

BACKGROUND

Cancer treatments such as high-dose chemotherapy and radiation destroy hematopoietic cells in the bone marrow, leaving the patients severely depleted of neutrophils and platelets. After such treatments, patients often spend several weeks in intensive care due to infections and fever resulting from neutropenia. Thrombocytopenia leads to reduced clotting and bleeding disorders requiring platelet transfusions. Lack of neutrophils and platelets is the leading cause of morbidity and mortality following these cancer treatments, and contributes to the high cost of cancer therapy.

Several methods are directed towards restoring the patient's immune system after therapy. Hematopoietic growth factors are administered after therapy to stimulate remaining stem cells to proliferate and differentiate into mature infection fighting cells. Although hematopoietic growth factors can shorten the total period of neutropenia, there remains a critical 10–15 day period immediately following therapy when the patient is severely neutropenic and thus infection prone. Even with growth factor stimulation, 10 to 15 days are required for the patient's stem cells to proliferate and progress through the various stages of differentiation leading to mature neutrophils. Megakaryocyte and platelet recovery requires an even longer time, generally greater than 15 days. Thus growth factor treatment leaves a gap during which the patient is deficient in infection fighting cells and blood clotting ability.

Post-therapy bone marrow transplantation can also ameliorate neutropenia after about 10–15 days. Since allogenic bone marrow transplantation is often complicated by Graft versus Host Disease, autologous bone marrow transplantation is preferred whenever practical. Bone marrow is harvested from the patient prior to therapy, frozen, and then thawed and transplanted back into the patient after therapy. Autologous bone marrow transplantation carries the risk that the transplanted bone marrow may harbor tumor cells. In any event, bone marrow does not contain sufficient mature neutrophils or their immediate precursors to restore the patient's immunity during the critical 10–15 day period after therapy.

A phenomenon known as "mobilization" has also been exploited to harvest greater numbers of stem/progenitor cells from peripheral blood to treat neutropenia. Mobilization occurs as a result of either chemotherapy, or administration of hematopoietic growth factors, or both. It is believed that hematopoietic stem cells in the bone marrow are "mobilized" into the peripheral blood stream as a natural result of the recovery of myelosuppressed bone marrow or in response to relatively large doses of hematopoietic growth factors. Growth factors used for mobilization include interleukin-3 (IL-3), granulocyte colony stimulating factor (G-CSF), granulocyte-macrophage colony stimulating factor (GM-CSF), stem-cell factor (SCF) and a recombinant fusion protein having the active moieties of both IL-3 and GM-CSF (Brandt, SJ, et al., N Eng J Med 318:169, 1988; Crawford, J, et al., N Eng J Med 325:164, 1991; Neidhart, J, et al., J Clin Oncol 7:1685, 1989). Mobilized peripheral blood stem cells are harvested after chemotherapy or growth factor treatment, and then reinfused into the patient following the next round of high dose chemotherapy or radiation. The reinfused stem cells then proliferate and differentiate in vivo, eventually to restore the patient's neutrophil and platelet population.

Combinations of the above approaches have succeeded in reducing the neutropenic period to about 9 days.

In order to obtain cells to treat patients during the early neutropenic period, differentiated hematopoietic cells were generated in vitro in the laboratory of the present inventors (Smith, S. L., et al., Experimental Hematology 21:870–877, 1993). Committed precursors of neutrophils were successfully generated in vitro using fetal bovine and horse serum-containing media. However, the potential for therapeutic use of the cells would be greatly enhanced if the cells were grown without animal sera or animal proteins in the culture medium.

Traditionally, animal serum supplementation was relied upon as a source for protein and growth factors in culture media formulations. Researchers have long sought media formulations free of animal proteins for the growth of therapeutic cells because of the potential for life-threatening immune reactions raised by infusion of foreign proteins. However, animal sera, and in particular fetal bovine sera, contain many unknown growth factors, certain factors being more or less important for each cell type. Even if every factor in fetal bovine serum were identified and chemically synthesized, it would still be a matter of trial and error and much experimentation to discover which factors promote the proliferation and differentiation of each cell type. In spite of the difficulty, researchers have succeeded in formulating serum-free media in which certain hematopoietic cells may be grown.

Serum-free media formulations containing bovine serum albumin and various hematopoietic growth factors were shown to promote the proliferation of murine bone marrow cells (Ponting, I.L.O., et al., Growth Factors 4:165–173, 1991; Merchauv, S., et al., Internatl J Cell Cloning 2:356–367, 1984;).

Thirteen different combinations of serum-free media proved disappointing as replacements for serum containing medium for the in vitro culture of human hematopoietic progenitors (Wu, Z-H., et al., Pathology 22:145–148, 1990). The effects of serum-free medium on the growth of leukemic cells were reported (Da, W. M., et al., Brit J Haematology 78:42–47, 1991). The growth of erythropoietic cells in serum-free medium was also reported (Lansdorp, P. M., et al., J Exp Med 175:1501–1509, 1992). All of the above serum-free formulations contained animal protein in the form of bovine serum albumin.

Animal proteins can be washed out of a cell composition by repeated rounds of centrifugation and resuspension until the animal proteins are undetectable by analytical methods. However, for greater convenience and greater assurance against immune reactions after infusion, it is desirable to use a therapeutic cell composition which was cultured in a completely animal-protein free medium.

SUMMARY OF THE INVENTION

The invention provides a method of treating a patient having a reduced population of neutrophils; this condition is typically caused by a myeloablative cancer treatment such as high dose chemotherapy. The method involves administering to the patient a serum-free, animal protein-free human cell composition of at least 25%, preferably at least 60% neutrophil precursors. Neutrophil precursors are promyelocytes, myelocytes, and metamyelocytes. Optionally, after administration of the neutrophil precursor composition, the cytokine G-CSF is administered to the patient. The neutrophil precursors differentiate rapidly in vivo to replenish the supply of infection-fighting mature neutrophils.

BRIEF DESCRIPTION OF THE FIGURES

FIG. 8 shows forward light scatter of the cells in flow cytometry; (a) control (b) anti-CD41a.

FIG. 12 shows the growth comparisons of megakaryocytes in different cultures.

FIG. 13 shows the effects of various cytokine combinations on megakaryocyte growth.

DETAILED DESCRIPTION OF THE INVENTION

Figure 1:
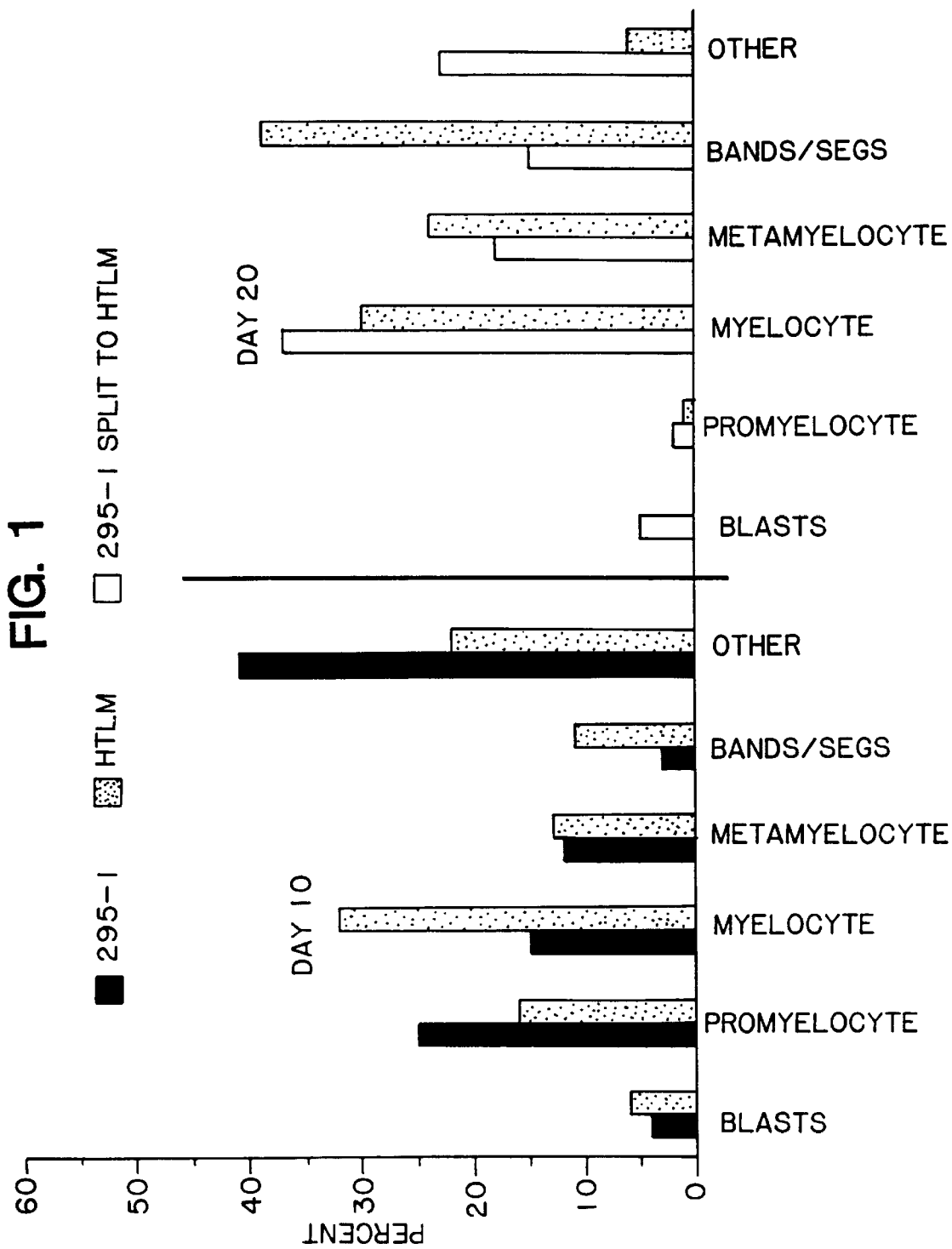
FIG. 1 depicts the differential cell count of cultures grown in serum-free medium (295-1), in serum-containing medium (HLTM), and cultures which were grown for 10 days in 295-1 and then transferred to HLTM for an additional 10 days.

The invention provides a method of treating a patient who is suffering from neutropenia. Typically, neutropenia is caused by myeloablative cancer therapy such as high dose chemotherapy (HDC). It is known to infuse allografts of the patient's own bone marrow or peripheral blood mononuclear cells (MNCs), or CD34+ selected stem/progenitor cells obtained before the myeloablative treatment, and then to support the patient with antibiotics until the reinfused stem/progenitor cells differentiate into mature infection fighting neutrophils. However, there is a considerable "neutropenic window" during which the patient must be hospitalized until his absolute neutrophil count (ANC) rises sufficiently so that his own neutrophils can take over the infection fighting job.

The method of the invention requires administering to the patient a serum-free, animal protein-free human cell composition enriched for human neutrophil precursors. Herein, the term "neutrophil precursors" refers to promyelocytes, myelocytes, and metamyelocytes indentified by morphological analysis of Wright-Giemsa-stained samples, as described herein. The cell composition contains at least 25% neutrophil precursors, preferably at least 60% neutrophil precursors. Optionally, the patient may be administered the cytokine G-CSF after infusion of the neutrophil precursor composition in order to promote rapid differentiation into mature neutrophils.

The absence of animal proteins in the cell suspensions is especially advantageous since animal proteins are known to cause immune reactions in humans. Moreover, a high proportion of the cells in the composition are at suitably advanced stages of differentiation so that soon after infusion they are expected to differentiate within the patient to form mature neutrophils, megakaryocytes and platelets.

This disclosure provides serum-free media formulations containing a base medium, corticosteroid, transferrin, insulin, cholesterol, ethanolamine, and human albumin.

The base medium may be any standard cell culture medium containing inorganic salts, vitamins, amino acids, and at least one energy source such as glucose or pyruvate. Preferably, the base medium contains a bicarbonate buffer and a pH indicator such as phenol red. The pH of the final medium is maintained at 6.8–7.4, preferably at about 7.2, by means of a controlled $O_2/CO_2$ gas atmosphere. The osmolarity of the basal medium is preferably in the range of 260–290 mOsm/Kg.

Hematopoietic growth factors are also necessary. Growth factors are selected from the following: interleukin-3 (IL-3), granulocyte-colony stimulating factor (G-CSF), granulocyte/macrophage-colony stimulating factor (GM-CSF), interleukin-6 (IL-6), interleukin-11 (IL-11), stem cell factor (SCF), interleukin-1 (IL-1), thrombopoietin and gamma interferon. Whole growth factors may be replaced by chimeric or fusion proteins having the active moieties of one or more factors. For instance, in place of IL-3 and GM-CSF, a single fusion protein having the active moieties of both IL-3 and GM-CSF may be used.

The growth factors are produced recombinantly in microorganisms or mammalian single-cell hosts, and have amino acid sequences either identical to or highly homologous with the active moieties of corresponding human growth factors. The factor is highly purified from any host proteins associated with it such that, when added to the herein provided media formulations, no host protein is detectable.

Given the disclosure herein, it will be apparent to one of skill in the art that growth factor combinations and concentrations may be manipulated to yield various results. For example, G-CSF and GM-CSF will enhance the production of neutrophils whereas thrombopoietin will enhance the production of megakaryocytes. The serum free media formulations provided herein are expected to further enable the identification of specific growth factor functions due to the absence of confounding factors from serum.

Herein, the term "serum-free" refers to a medium formulation which does not include any form of whole serum, neither animal nor human. Herein, a protein which has been purified from other serum components is considered serum-free.

Human serum albumin (HSA) provides a source of protein in the media. It is generally believed that protein is required to provide a viscosity similar to that of blood so that hematopoietic cells may thrive. Moreover, protein acts as a substrate for proteases which might otherwise digest cell membrane proteins. Albumin is thought to act as a carrier for trace elements and essential fatty acids. HSA is greatly advantageous over protein derived from animals such as bovine serum albumin (BSA) due to the reduced immunogenic potential of HSA. The HSA may be derived from pooled human plasma fractions, or may be recombinantly produced in such hosts as bacteria and yeast, or in vegetable cells such as potato and tomato. Preferably, the HSA used in the present formulations is free of pyrogens and viruses, and is approved by regulatory agencies for infusion into human patients. The HSA may be deionized using resin beads prior to use in the media.

Transferrin and insulin used in these serum-free media formulations may be derived from animal sera, but it is most preferable to use products which are recombinantly synthesized. It is understood that when transferrin and insulin are derived from an animal source, they are purified to remove other animal proteins, and thus are at least 99% pure. Transferrin is used in these formulations at only 25–125 µg/ml, while insulin is used at only 1–25 µg/ml. Therefore, any trace of animal protein other than insulin or transferrin in the medium is non-detectable using standard techniques such as HPLC and gel electrophoresis. Herein, the term "essentially free of animal proteins" refers to a medium formulation or a cell suspension in which no animal proteins other than transferrin or insulin are detectable. The term "animal" is understood to exclude microorganisms and humans. Preferably, the transferrin and insulin are genetically engineered proteins produced by microorganisms such as bacteria and yeast. Most preferably, the amino acid sequences of the recombinant transferrin and insulin are identical to or highly homologous with those of humans. Thus, the most preferable serum-free media formulations herein contain no animal-derived proteins and do not have even a non-detectable presence of animal protein.

The corticosteroid component may be any naturally occurring or synthetic glucocorticoid hormone, preferably hydrocortisone at a concentration of 1–10 µM. The corticosteroid may also be dexamethasone, methylprednisone, or other glucocorticoids approved for clinial use.

Cholesterol may be chemically synthesized or purified from human serum. Cholesterol is used in the present media formulations at a concentration of 0.01–0.1 mg/ml, most preferably at 0.05 mg/ml.

Surprisingly, it was discovered that ethanolamine added to serum free media in the range of 50–200 µM, preferably 100 µM, greatly increased the proliferation and development of neutrophil and megakaryocyte precursors. Ethanolamine, also known as β-aminoethyl alcohol, is a viscous, hygroscopic liquid which is commonly used as a surfactant in the manufacture of pharmaceuticals. The exact function of ethanolamine in the present media formulations is not known, however this does not diminish the importance of the discovery of its beneficial effects, especially within the context of the specific media formulations provided herein.

In the most ideal system, serum-free media are made fresh each day and continuously refreshed in the cultures. However, reducing agents such as α-monothioglycerol and β-mercaptoethanol, which are thought to diminish free-radical formation, may be added to the serum-free media formulations to enhance stablility during storage times of up to 20 days or longer. Reducing agents may also be helpful when the media formulations are used in static culture and refreshed only after several days of use. Antibiotics such as gentimicin may also be added to the media as a precaution against bacterial infection of the cultures.

Media formulations containing the above reagents, known herein as media "295-1", were found to be optimal for the development of megakaryocyte precursors within a population of neutrophil precursors, as will be described below. However, it was discovered that the addition of other lipids to the above essential reagents could enhance the proliferative potential of neutrophil precursors. Optionally, triglycerides and/or phospholipids are included as additional sources of lipid. A preferable source of lipid is a sterile, non-pyrogenic fat emulsion prepared from soybean oil and egg yolk phospholipids, typified by Intralipid® (Kabi Pharmacia). Such a preparation preferably contains a mixture of neutral triglycerides of predominantly unsaturated fatty acids such as linoleic, oleic, palmitic, linolenic, and stearic acid. Such a preparation may also contain phosphatidylethanolamine and phosphatidylcholine from egg yolk. Another source of lipid is a human plasma fraction precipitated by ethanol and preferably rendered virus-free by pasteurization. For example, a growth-enhancing media supplement, Nutrimax™ (Baxter Hyland), is derived from Cohn's fraction $IV_4$ and contains triglycerides as well as cholesterol. When a cholesterol-containing lipid preparation is used, it may substitute for the cholesterol in the 295-1 formulation above provided the lipid preparation supplies cholesterol at a final concentration of at least about 30 µg/ml.

Commercially available serum-free media formulations such as EX VIVO® may also be utilized provided they are supplemented with human albumin and the requisite growth factors.

Using the above serum-free formulations, optimal populations of neutrophil and megakaryocyte precursors are generated in vitro. The cells originate either from bone marrow, from cord blood, or from peripheral blood. Bone marrow samples may be obtained either from normal donors or from patients. Umbilical cord blood is obtained after normal gestations. Peripheral blood is obtained either from normal donors or from cancer patients. In some cases, cancer patients are treated with hematopoietic growth factors to "mobilize" or stimulate their stem cells to move from bone marrow to their peripheral blood stream, thus greatly increasing the number of stem/progenitor cells in their peripheral blood samples.

Herein, the term "stem/progenitor cell" refers to a hematopoietic cell having the CD34+ cell surface antigen (stem cells and colony-forming units). In non-mobilized peripheral blood, the number of CD34+ cells comprises only about 0.1% of total leukocytes. Mobilization brings the number of CD34+ cells up to about 1–4% of total leukocytes. In cord blood, CD34+ cells comprise about 0.1–1% of total leukocytes. Normal bone marrow typically contains only 1–2% CD34+ cells.

White blood cells (leukocytes) are first separated from the samples of bone marrow or cord or peripheral blood by standard methods such as centrifugation through a gradient. A leukocyte population from bone marrow generally contains only about 10–15% myeloblasts and promyelocytes (Geigy Scientific Tables, Vol 3, C. Lentner, ed. Ciba-Geigy, Basel, Switzerland, 1984). Mature megakaryocytes in bone marrow, as recognized by Wright-Giemsa staining, comprise only about 0.05% of the leukocyte population, while immunostaining specific for megakaryocyte lineage cells labels up to about 0.2%. Since, in a healthy individual, neutrophil and megakaryocyte precursors differentiate fully in the bone marrow, a precursor is only very rarely discovered in normal blood.

After separation, leukocytes may be cultured directly in serum-free medium. Preferably, however, stem/progenitor cells are separated from the leukocyte population by positive selection. Positive selection of stem/progenitor cells may be based on their binding to an antibody specific for CD34+, followed by separation of antibody-bound stem/progenitor cells using paramagnetic beads (Hardwick, RA, et al., *J Hematother* 1:379–386, 1992; Smith, SL, et al., supra).

Positively selected stem/progenitor cells are placed in culture at densities ranging from 5,000 to 100,000 cells/ml, preferably at 10,000 cells/ml. Any standard tissue culture flasks or bags may be used in either a static or a perfusion culture system (Koller, MR, et al., *BIO/TECHNOLOGY* 11:358–363; Emerson, SG, et al., PCT W092/11355). When a static culture system is used, the cells are fed at intervals of 5 to 7 days to replenish nutrients and remove wastes.

Cells are cultured in serum-free medium for 7–14 days, more preferably 9–12 days, at which time the cell suspension contains a suitable population of neutrophil and megakaryocyte precursors for use in the treatment of neutropenia and thrombocytopenia. When serum-free medium formulation 295-1 is used, the cell population contains at least about 16% neutrophil precursors and at least about 1% megakaryocyte precursors. Preferably, the cell population contains over 30% neutrophil precursors, more preferably over 60% neutrophil precursors. The neutrophil precursor population is composed of promyelocytes, neutrophilic myelocytes, and neutrophilic metamyelocytes, which are the precursors of mature banded and segmented neutrophils (Marmont, AM., et al., IN "Neutrophils", *Atlas of Blood Cells, Function and Pathology,* Eds. Zucker-Franklin, D., et al., 2nd Edition, pp. 159–190; Jandl, JH 1987 *Blood, Textbook of Hematology,* Little, Brown & Co., Boston/Toronto, pp.441–480).

Flow cytometric analysis of the 10-day serum free cultures was performed to determine the cells' phenotypes based on labeling with cell surface antigens. Cells which are positive for the CD15 antigen and negative for the CD11b antigen (CD15+/CD11b−) have been shown by morphological analysis to be predominantly myelocytes and promyelocytes (Smith, SL, et al., supra). Cells which were CD15+/CD11b+ were previously shown to be predominantly mature segmented neutrophils when they were isolated directly from blood or from cultures grown in serum-containing media. However, CD15+/CD11b+ cells from the serum-free cultures described herein were predominately myelocytes and metamyelocytes, with less than 5% band and segmented forms. The 10-day serum-free cultures of the present invention were shown to contain 20–60% CD15+/CD11b− cells. When the cultures were transferred at day 10 from serum-free to serum containing medium, the phenotypes were seen to progress to predominantly mature forms as identified by CD15+/CD11b+ labeling (FIG. 5c) combined with morphological analysis.

Fortuitously, it was discovered that cultures grown in serum-free 295-1, without added lipids, contained a high proportion of megakaryocyte precursors. Herein, the term "megakaryocyte precursor" refers to a nucleated cell which expresses the platelet/megakaryocyte specific glycoprotein IIb/IIIa, also known as "CD41a", as identified by immunostaining and/or flow cytometry. The megakaryocyte precursor population is composed mainly of promegakaryoblasts and megakaryoblasts (Long MW, *Stem Cells* 11:33–44, 1993; Paulus, JM, "Platelet kinetics", in: Williams, WJ, et al., (eds), *Hematology,* McGraw-Hill, New York: 1251–1260, 1990).

Preferably, the megakaryocyte precursor component of the serum-free 9–12 day cultures comprises about 1% of the total cells, more preferably at least about 3% of the total cells, most preferably greater than 8% of the total cells. Surprisingly, these results in serum-free medium 295-1 were superior to those obtained in the control, serum-containing medium. Culture in serum-free medium yielded 3–22 times the number of megakaryocte precursors as compared with control, which suggested that the serum component may have an inhibitory effect on megakaryocyte precursor growth. Moreover, this enrichment of the cell population for megakaryocyte precursors in liquid culture represents a great advance over previous reports of megakaryocyte growth in vitro (Nakef, A., et al., *Ser Heamat* 8:4, 1975; Metcalf, D., et al., *PNAS* 72:1744, 1975; Dexter, T. N., et al., *J Cell Physiol* 91:335, 1977).

This discovery of a cell suspension greatly enriched for megakaryocyte precursors enables the effective treatment of various types of thrombocytopenia in addition to those caused by cancer therapy. Thus, the herein provided cell suspensions may replace platelet infusions in the treatment of thrombocytopenia. Moreover, the co-existence of a high proportion of megakaryocyte precursors with neutrophil precursors renders these serum-free cell suspensions ideal for the co-treatment of thrombocytopenia and neutropenia.

When the above cell population is administered to a patient following ablative therapy, it is expected that the administered cells will further differentiate in vivo to form mature neutrophils and megakaryocytes, which ultimately form platelets. This expectation is based upon the discovery that when this cell population is switched to serum-containing medium for a further 10 days of culture, the population advances to more mature neutrophilic forms (FIG. 1). Moreover, when placed in a fibrin-clot assay, the megakaryocyte precursors were observed to form mature megakaryocytes and release platelets. The results from these assays suggest that cells from the serum-free cultures can undergo further maturation after they are returned to in vivo conditions.

One of the primary advantages of the 7–14 day serum-free cell culture lies in its population of more mature neutrophil and megakaryocyte precursors, as described above. However, another advantage of this cell culture lies in its small population of earlier cell types, i.e. "progenitors", which are capable of a number of successive rounds of proliferation and differentiation. The daughter cells of these progenitors are expected to follow the precursors in maturation to provide a later population of neutrophils and megakaryocytes, thereby extending the duration of effective treatment possible from an infusion of the original cell suspension.

Progenitors within the neutrophilic lineage are identified as colony-forming units (CFU) and cluster-forming units (clFU) The term CFU is herein defined as a single cell which, when plated in a serum-containing methylcellulose culture for 14 days, proliferates to form a closely associated group of 50 or more cells (a "colony"). Under the same conditions, a clFU forms a group of fewer than 50 cells (a "cluster"). Colonies are further defined by the cell type(s) they contain, as identified by Wright-Giemsa staining (Zucker-Franklin, et al., supra). The colonies which are expected to ultimately form mature neutrophils and monocytes are designated "granulocyte/macrophage" or GM. The clusters are composed of early granulocyte precursors and macrophages, with the granulocytic types predominating.

It was discovered that the addition of a lipid to the 295-1 serum-free formulation could increase the percentage of CFU and clFU in the population. As demonstrated in colony-forming assays, this cell population preferably contains about 0.5 to 3.0% CFU and clFU combined. In the above cell population, GM-CFU preferably comprise about 5–50% of the total CFU/clFU. The cells within the clusters are more differentiated than the cells within the GM colonies. Thus, the clFU within the population are expected to provide a bridge of committed precursors before the GM-CFU have gone through a sufficient number of divisions and stages of differentiation to replenish the precursor population. Preferably, in the above cell population, the clFU comprise about 40–60% of the total CFU/clFU.

Compared to neutrophilic CFU and clFU, a colony of cells of the megakaryocyte lineage may contain fewer cells due to their unique form of differentiation. When plated in a fibrin-clot culture for 14 days, a megakaryocyte burst forming unit (MK-BFU) proliferates to form a group of 40 or more megakaryocytes and shows a focal development of many colonies. Thus the MK-BFU is regarded as the early megakaryocyte progenitor. A megakaryocyte colony forming cell (MK-CFC) proliferates to form 2 to 39 megakaryocytes and is regarded as the megakaryocyte progenitor more mature than the MK-BFU. The single megakaryocyte forming unit (S-MK) can only undergo endomitosis (DNA duplication without cell division) and form a single polyploid cell in the colony culture. The S-MK is thus regarded as more mature than the MK-CFC. As demonstrated by specific immunostaining in fibrin clot assays, MK-BFU represent 30–57% of the total cells in 5–7 day cultures capable of megakaryocyte burst/colony formation. By day 12 in serum-free culture, all the MK colony forming units have progressed to MK-CFC or S-MK. These results in fibrin clot assays confirm that the megakaryocyte precursors grown in serum-free liquid culture for 5–12 days are capable of differentiation to mature megakaryocytes.

The serum-free cell suspensions provided herein can be administered to a patient in an amount sufficient to abrogate neutropenia and thrombocytopenia following ablative cancer therapy. The enrichment of neutrophil and megakaryocyte precursors in these cell suspensions allows the administration of an effective therapeutic number of desired cells with fewer total cells returned to the patient. An exemplary protocol for the infusion of the cell compositions is provided in Example 13 below. However, persons skilled in the art of hematopoietic cell transfusion will be able to determine the optimal quantity and conditions for administration of the cell suspensions based on their own clinical experience and using guidelines from literature on stem cell infusions (Spitzer, G., et al., *Blood* 55:317–323; Douay, et al., *Exp Hematol* 14:358–365, 1986).

The following experimental examples are intended to illustrate the present invention without limiting its scope.

EXAMPLE 1
Serum-free media formulations
Serum free media were formulated as follows. Optimum concentrations were determined by separate titrations based on cell proliferation.

"295-1" Formulation

Isocove's Modified Dulbecco's medium (IMDM, Sigma) or McCoy's 5A (Sigma)
HEPES buffer, 10–25 mM, optimum 25 mM
hydrocortisone, 1–10 $\mu$M, optimum 200 ng/ml
transferrin (human holo) (Sigma), 25–125 $\mu$g/ml, optimum 75 $\mu$g/ml
insulin (human recombinant, Novo Nordisk, Princeton, N.J.),
1–25 $\mu$g/ml, optimum 10 $\mu$g/ml
selenium, 0.017–5 ng/ml, optimum 5 ng/ml
alpha-monothioglycerol, 10–160 $\mu$M, optimum 216 ng/ml
beta-mercaptoethanol, 20–100 $\mu$M, optimum 50 $\mu$M
gentamicin, 10–50 $\mu$g/ml, optimum 50 $\mu$g ml
recombinant human hematopoietic growth factors selected from rIL-3 (Amgen, Thousand Oaks, Calif.), rG-CSF (Amgen), rGM-CSF (Amgen), rSCF (Genzyme, Boston, Mass.), and PIXY-321 (a recombinant protein composed of the active moieties of IL-3 and GM-CSF, Immunex, Seattle, Wash.). Growth factor types and concentrations are stated for each experimental example below.
cholesterol, (Sigma or Miles), 30–60 $\mu$g/ml, optimum 60 $\mu$g/ml
ethanolamine, 50–200 $\mu$M, optimum 100 $\mu$M
human albumin (Baxter Hyland, Duarte, Calif.), 0.1–25 mg/ml, optimum 10 mg/ml. Human albumin was used both as received from supplier and after deionization with resin beads. The deionization procedure was carried out at 4° C. by stirring 100 ml albumin (human) 25% solution Buminate (Baxter Hyland Cat no 142-6425) with 0.5–1.0 g of mixed bead resin (AG 501-X8 (D) Biorad, Richmond, Calif.) until the resin beads turned from blue to yellow. The solution was centrifuged at 1000 rpm for 5 minutes to pellet the beads. The albumin solution was decanted, and the stirring procedure with fresh resin beads was repeated. The entire procedure was repeated until the beads no longer changed color (generally, 4 times).

In designated experiments, three different types of lipid preparations were added to formulation 295-1:

1. Lipid derived from a human plasma fraction (Pentex® Ex-Cyte®, Miles Inc., Kankakee, Ill.; cholesterol, 4.96 mg/ml; triglycerides, 1.67 mg/ml) was used at dilutions from 1:50–1:500, optimum 1:100.
2. Lipid derived from ethanol precipitated Cohn's fraction IV$_4$ from pooled human plasma, pasteurized to kill viruses (Nutrimax™, Baxter Hyland, Duarte, Calif.), at 0.2–5 mg/ml.
3. Lipids derived from soybean oil and egg yolk (Intralipid®, Kabi Pharmacia, Clayton, N.C.; neutral triglycerides with fatty acid residues comprising 50% linoleic, 26% oleic, 10% palmitic, 9% linolenic, and 3.5% stearic; phospholipids comprising primarily phosphatidylcholine and phosphatidylethanolamine), at 0.03–2%, optimum 1%.

Stock solutions of each lipid were prepared in ethanol at a dilution of 1:10. Optionally, Intralipid® was sonicated in a test tube for 30 minutes.

Control serum-containing medium (HLTM) was composed of the above base media, standard supplements and growth factors, plus 12.5% fetal bovine serum and 12.5% horse serum (Sigma).

EXAMPLE 2
Preparation of hematopoietic stem/progenitor cells
Mononuclear cells were obtained from samples of bone marrow, cord blood, or peripheral blood. Normal individuals provided the bone marrow and cord blood. The peripheral blood cells were obtained from cancer patients whose hematopoietic cells had been "mobilized" into their peripheral blood from their bone marrow by the administration of hematopoietic growth factors (Brandt, SJ, et al., supra; Crawford, J., et al., supra; Neidhart, J., et al., supra). The cells in the samples were separated by centrifigation through Histopaque® (Ficoll® Hypaque®, Sigma) and the mononuclear cells from the interface band were collected (Smith, S. L., et al., *Exp Hematol* 21:870–877, 1993).

The suspensions of mononuclear cells were enriched for stem/progenitor cells by positive selection of CD34+ cells using magnetic beads as follows. The mononuclear cells were first sensitized for 30 minutes on ice with 0.5 μg of anti-CD34 antibody per $10^6$ cells [anti-CD34 #9069 prepared by serum-free cell culture (Baxter Hyland, Hayward, Calif.) and purified by protein G affinity chromatography (Baxter Immuntherapy Division)]. The cells were then washed 3 times by centrifugation in IMDM to remove unbound antibody and mixed with sheep antimouse $IgG_1$-Fc coated magnetic beads at a bead-to-cell ratio of 1:1. The mixture of beads and cells was then rotated for 30 minutes at 4° C. The bead/cell complexes were then isolated using a magnetic tube holder. After a series of washes, CD34+ cells were released from the beads by adding 50 U/ml of Chymodiactin® (Bootes Pharmaceutical, Lincolnshire, Ill.) in RPMI 1640 (Sigma) and incubating for 15 minutes in a 37° C. water bath. The cells released from the beads were then evaluated for CD34+ purity by staining with the FITC-8G12 monoclonal antibody to CD34 (Baxter Immunotherapy Division, Irvine, Calif.) for 15 minutes on ice and quantitated with a FACSan® flow cytometer (Becton Dickenson, San Jose, Calif.) as described (Smith, S. L., et al, supra).

EXAMPLE 3

Culture of hematopoietic cells in serum-free media

Enriched preparations of CD34+ cells were cultured in serum-free media at initial concentrations of $5 \times 10^3$–$1 \times 10^5$ cells/ml in either polystyrene flasks or plastic bags. Tissue-culture-treated flasks, as well as non-treated flasks of 25, 75 and 150 $cm^2$ (Corning, Corning, N.Y.) were used. The ethylvinyl acetate (EVA) gas-permeable plastic bags were type PL269 of 250, 500, and 1000 ml capacity (Baxter Fenwal, Deerfield, Ill.). The 250 ml bags were filled with 20–60 ml, the 500 ml bags were filled with 60–100 ml, and the 1000 ml bags were filled with 100–400 ml of cell suspension. The cultures were placed in a 5% $CO_2$/5% $O_2$, 37° C. high humidity incubator for the times indicated in the examples below. The cultures were fed at intervals of 5–7 days, with dilutions of 1:2 or 1:4.

The concentration of nonadherent cells in the cultures was determined by diluting 0.5 ml from the culture in 9.5 ml 10% cetrimide (Sigma) and counting on a Coulter ZBI (Coulter Electronics, Hialeah, Fla.).

EXAMPLE 4

Assessment of growth of neutrophil precursors in serum-free medium

The cell cultures of Example 3 were sampled at indicated days in culture, stained by the Wright-Giemsa method, and differentially counted according to morphological characteristics (Marmont, A. M., et al. "Neutrophils", in *Atlas of Blood Cells,* Eds. Zucker-Franklin, D., et al., 2nd Edition, pp.159–190; Jandl, J. H. (1987) *Blood, Textbook of Hematology*, Little, Brown & Co., Boston/Toronto, pp.441–480). FIG. 1 depicts the differential cell count of a typical cell culture grown in serum free medium formulation 295–1 (example 1) compared with growth in serum-containing medium ("HLTM"). Hematopoietic growth factors were added to both media as follows: IL-3 at 1000 U/ml, G-CSF at 500 U/ml, GM-CSF at 500 U/ml, and SCF at 20 ng/ml. At day 10 of culture, samples of cells which had been grown in serum-free medium were transferred to serum-containing medium for an additional 10 days.

Figure 2:
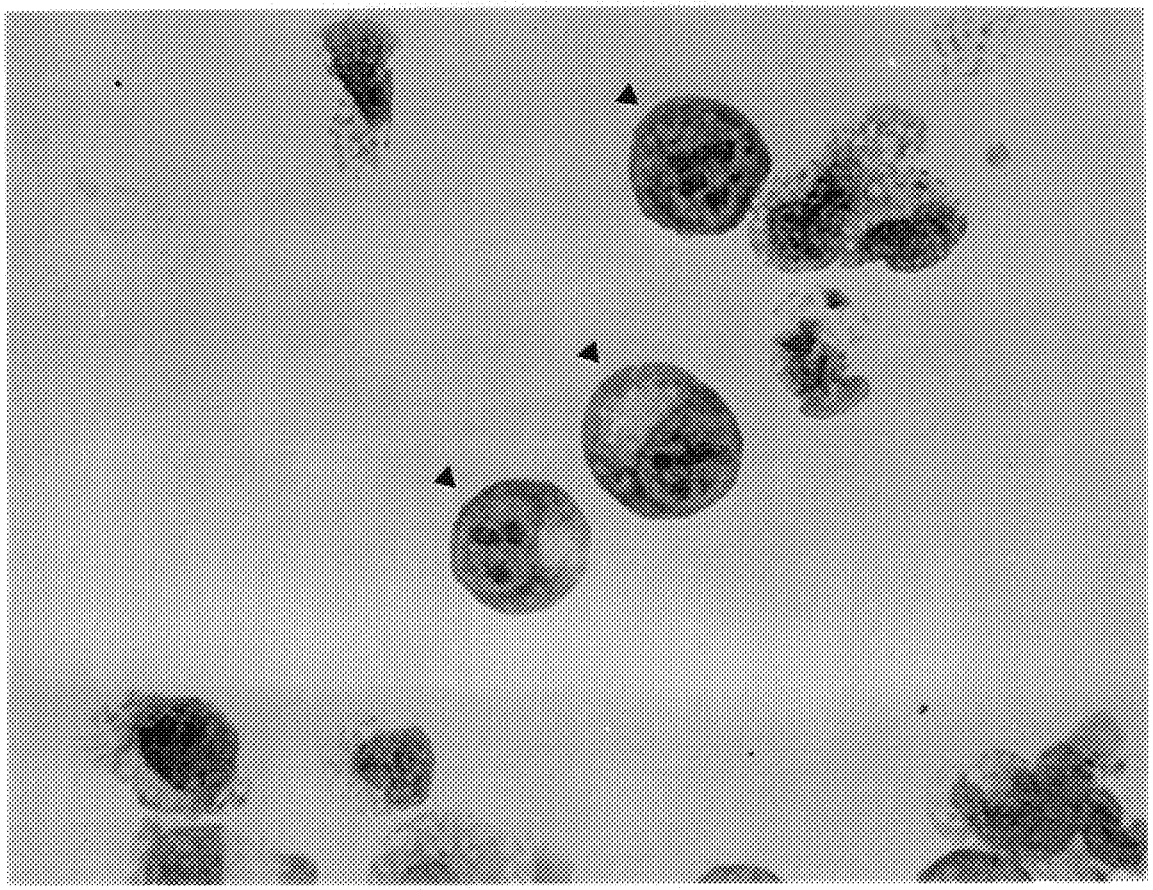
FIG. 2 shows blast cells (solid arrows) in a 10 day serum-free culture.

Examples of the morphology of various cell types are shown in the following figures:

FIG. 2. Blast cells (solid arrows).

Figure 3:
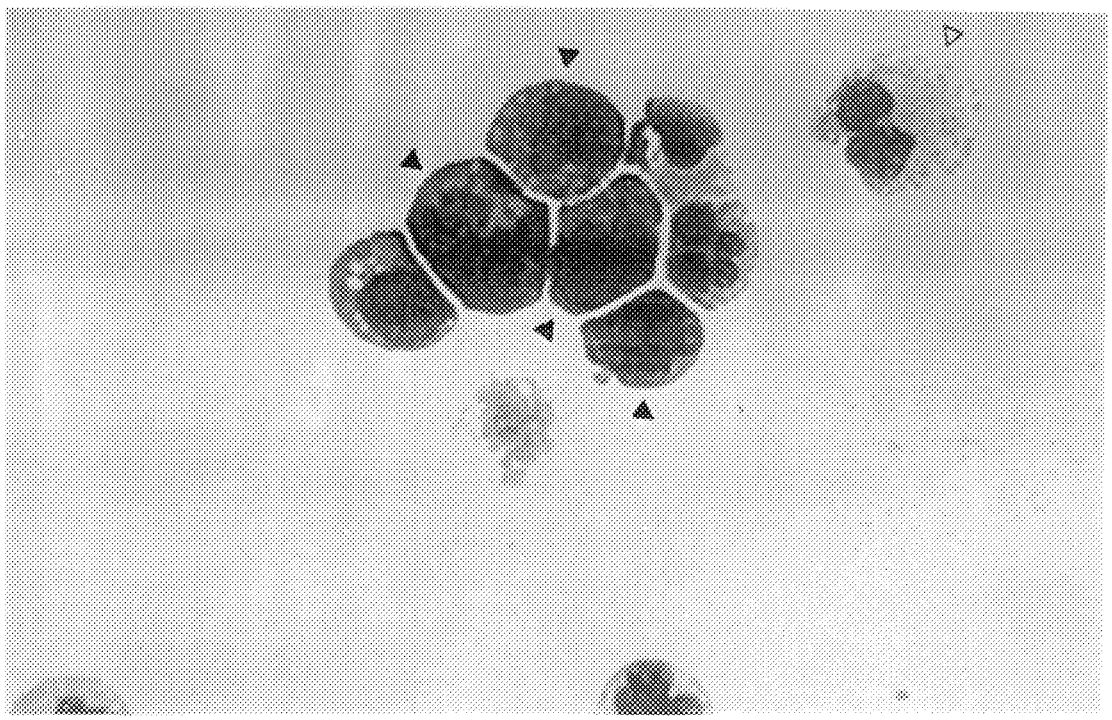
FIG. 3 shows promyelocytes (solid arrows) and a neutrophilic metamyelocyte (hollow arrow) in a 10-day serum-free culture.

FIG. 3. Promyelocytes (solid arrows) and neutrophilic metamyelocyte (hollow arrow).

Figure 4:
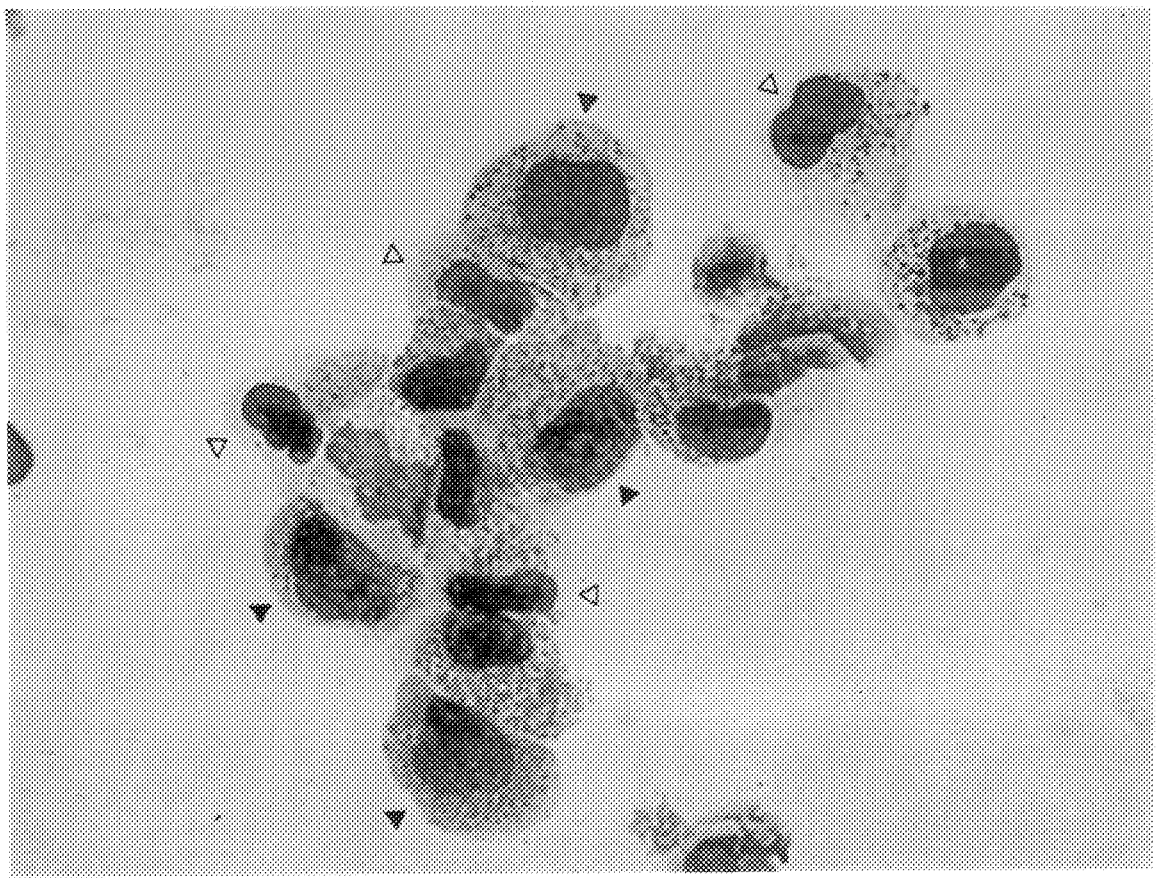
FIG. 4 shows neutrophilic myelocytes (solid arrows) and neutrophilic metamyelocytes (hollow arrows) in a 10 day serum-free culture.

FIG. 4. Neutrophilic myelocytes (solid arrows) and neutrophilic metamyelocytes (hollow arrows).

Band forms and segmented neutrophils ("Bands/Segs", FIG. 1), the most mature neutrophilic cells, were readily recognized according to standard criteria (Marmont, A. M., et al., supra). The category designated "Other" in FIG. 1 includes monocytes, macrophages, and megakaryocyte precursors which are not identifiable by Wright-Giemsa staining. Monocytes and macrophages were identified as described in the Atlas of Blood Cells (supra, Johnston, RB, Jr., The mononuclear phagocyte system, pp.321–377). Megakaryocyte precursors were identified by immunocytochemical staining as described below. Mast cells, which can be identified by toluidine blue staining of their heparin granules, represented less than 0.01% of the total cell population.

Differential cell counts varied among experiments due to the wide differences among individual samples obtained from various sources such as normal bone marrow, cord blood, and "mobilized" peripheral blood cells from cancer patients.

Typically, however, differential neutrophilic cell counts of cultures grown for 9–12 days in serum-free medium were comparable to cultures from the same samples grown in serum-containing medium. Serum-free cell cultures between 9–12 days in vitro typically contained 10–40% blast cells, 15–30% promyelocytes, 10–25% neutrophilic myelocytes, 10–40% neutrophilic metamyelocytes, and 10–22% "other" (monocytes, macrophages, and megakaryocyte precursors).

When cells were cultured in serum-free medium for 10 days, then transferred to serum-containing medium for an additional 10 days, they differentiated to more mature forms (FIG.1). Their differential neutrophilic cell counts at day 20 were comparable to the cells which had been grown for the entire 20 days in serum-containing medium.

EXAMPLE 5

Neutrophil precursors crown in serum-free medium: Phenotype identified by flow cytometry At 10 and 20 days of culture, aliquots of $1-2 \times 10^5$ cells were removed from the culture vessels and washed 1–2 times in phosphate buffered saline containing 0.05% bovine serum albumin and 0.1% azide (PAB). The cells were then labeled with CD15 (LeuM1) FITC-conjugated and CD11b (Leu5) PE-conjugated monoclonal antibodies (Becton Dickenson) for 10 minutes on ice. Following 1 additional wash in PAB, the cells were suspended in 1 ml PAB and analyzed by flow cytometry for coexpression of CD15 and CD11b.

Figure 5A:
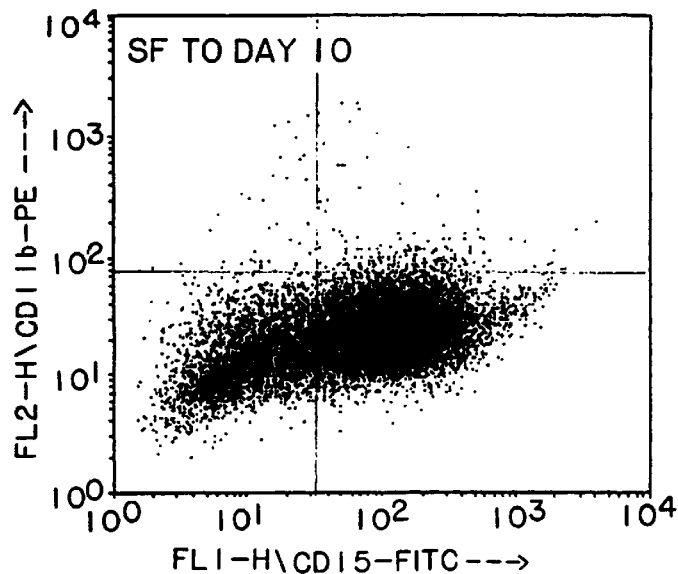
FIG. 5 shows the cell phenotypes as determined by flow cytometry.
Figure 5B:
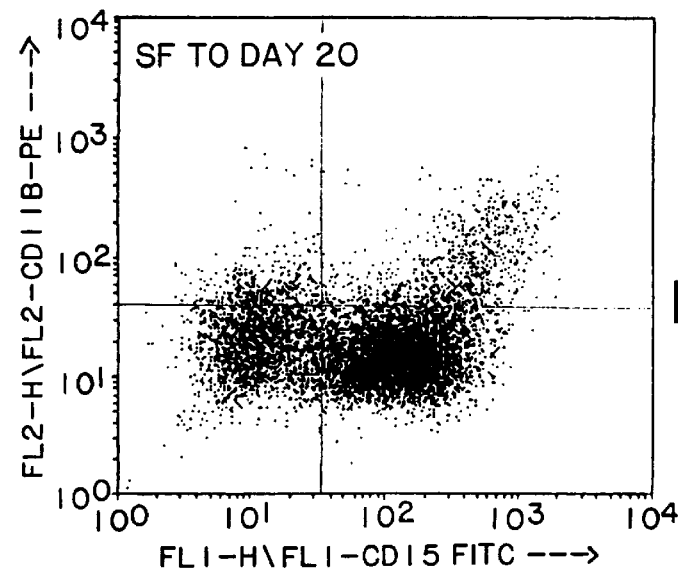
Figure 5C:
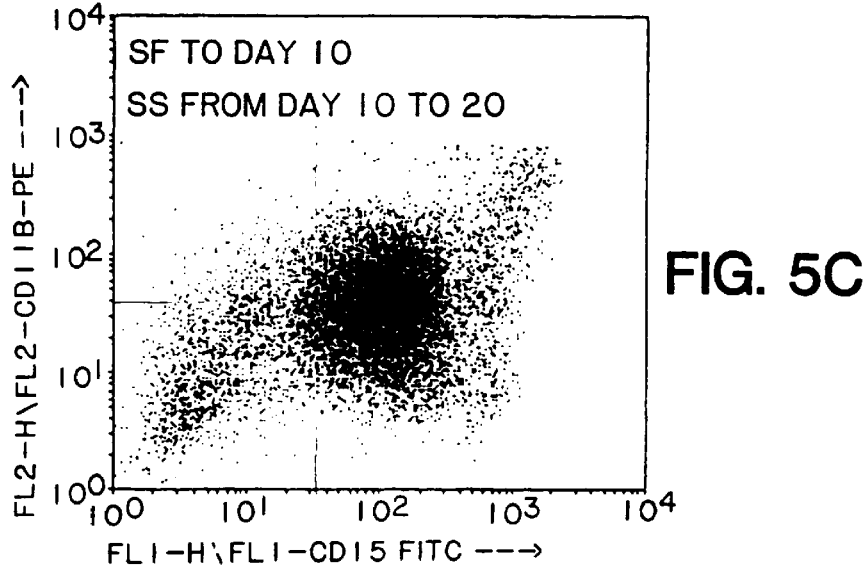

At day 10, the CD15+CD11b– phenotype comprised 20–60% of the cells in serum-free cultures, which was similar to the day 10 profile of serum-containing cultures (FIG. 5a, lower right quadrant). At day 20, cultures which had been maintained in serum-free media still contained predominantly the CD15+CD11b– phenotype (FIG. 5b). In contrast, at day 20, cultures which had been transferred from serum-free to serum-containing media at day 10 contained 70–100% differentiated cells of the CD15+11b+ phenotype, similar to the phenotypic profile of cultures which had been grown in serum-containing media for the entire 20 days (FIG. 5c).

Cells which were CD15+/CD11b– were sorted by FACS cell sorting and identified morphologically as neutrophilic precursors in the promyelocyte and myelocyte stages of differentiation (Smith, SL, et al., supra). Cells which were CD15+/CD11+ were sorted and identified as the more mature forms, i.e. metamyelocytes, band forms, and segmented neutrophils.

EXAMPLE 6

Colony forming units and cluster forming units in serum free cultures

Cells were grown in various media formulations using the following growth factors: IL-3 at 300 U/ml, G-CSF at 300 U/ml, GM-CSF at 300 U/ml, and SCF at 20 ng/ml.

Figure 6:
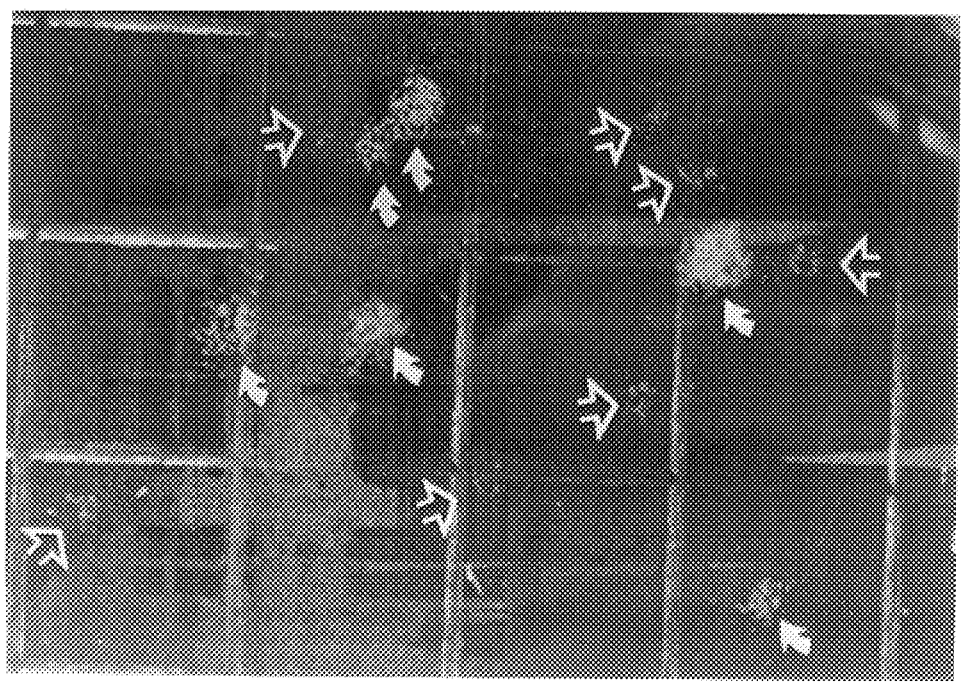
FIG. 6 shows a typical field of colonies (solid arrows) and clusters (hollow arrow).

At day 0 and at 10 days of culture, colony assays were set up in methyl-cellulose containing IMDM, 30% FBS (Sigma), 7% Leptalb 7 (Armour Pharmaceuticals, Kankakee, Ill.) and recombinant growth factors at 150 U/ml rIL-3, 200 U/ml rGM-CSF, 150 U/ml rG-CSF, 160 U/ml rIL-6 and 10 U/ml erythropoietin (Amgen, Thousand Oaks, Calif.). Colony assays were set up in triplicate at 5 to $10 \times 10^3$ cells/ml in 35 ml dishes (Nunc) and scored following 14-day incubation in 5% $CO_2$/5% $O_2$ at 37° C. Colonies were defined as groups of greater than 50 cells, and clusters were defined as groups of fewer than 50 cells (see FIG. 6). The colonies were identified macroscopically as either CFU-GM, macrophage (CFU-M), burst-forming unit erythroid (BFU-E) or mixed (CFU-Mix) (myeloid and erythroid) with periodic morphological verification of plucked colonies using Wright-Giemsa staining. Results are shown in Tables 1–4 below.

Key for Tables 1–4

P.I.=proliferation index (total cells at day 10/total cells at day 0)

GM I.=granulocyte/macrophage-colony forming index (GM colonies formed from 10 day culture/GM colonies formed from day 0 suspension).

Mac I.=macrophage colony forming index

BFUE I.=burst forming unit-erythroid index

Mixed I.=mixed colony forming index

Cluster I.=cluster forming index

PB=peripheral blood sample

B.M.=bone marrow sample

CFU=colony-forming unit; CE =cloning efficiency

TABLE 1

| | PB1 Culture Medium | P.I. Day 10 | GM I. Day 10 | Mac I. Day 10 | BFUE I. Day 10 | Mixed I. Day 10 | Cluster Day 10 |
|---|---|---|---|---|---|---|---|
| Deionized Albumin | Base | 11.9 | 1.5 | 0.0 | 7.6 | 0.0 | 15.5 |
| | + Intralipid | 12.6 | 3.9 | 0.0 | 8.5 | 0.0 | 18.9 |
| | + Ethanolamine | 9.9 | 0.7 | 0.0 | 0.5 | 0.0 | 12.9 |
| | + Intra./Ethan. | 10.3 | 1.4 | 0.3 | 0.4 | 0.0 | 8.2 |
| Non-Deionized Albumin | Base | 13.2 | 1.4 | 0.7 | 7.0 | 2.0 | 25.1 |
| | + Intralipid | 6.7 | 0.5 | 0.0 | 1.1 | 0.0 | 2.0 |
| | + Ethanolamine | 7.3 | 2.0 | 0.6 | 8.5 | 2.2 | 5.8 |
| | + Intra./Ethan. | 10.3 | 3.3 | 0.8 | 16.6 | 11.8 | 12.4 |
| Serum Controls | IMDM + 25% | 14.4 | 5.8 | 1.6 | 14.5 | 2.2 | 20.2 |
| | HLTM | 14.7 | 4.9 | 0.8 | 6.2 | 2.2 | 27.9 |
| | PB2 Culture Medium | P.I. Day 10 | GM I. Day 10 | Mac I. Day 10 | BFUE I. Day 10 | Mixed I. Day 10 | Cluster Day 10 |
| Deionized Albumin | Base | 9.9 | 0.5 | 0.0 | 0.4 | 0.0 | 2.8 |
| | + Intralipid | 33.3 | 0.5 | 0.2 | 0.6 | 0.1 | 8.2 |
| | + Ethanolamine | 26.2 | 7.5 | 0.9 | 1.7 | 0.4 | 19.0 |
| | + Intra./Ethan. | 23.7 | 5.2 | 2.5 | 1.1 | 0.7 | 53.7 |
| Non-Deionized Albumin | Base | 4.2 | 0.1 | 0.0 | 0.1 | 0.0 | 0.6 |
| | + Intralipid | 23.7 | 2.4 | 0.3 | 1.2 | 0.3 | 9.5 |
| | + Ethanolamine | 15.1 | 0.7 | 0.1 | 0.6 | 0.1 | 6.5 |
| | + Intra./Ethan. | 33.3 | 0.5 | 0.0 | 0.2 | 0.0 | 1.9 |
| Serum Controls | IMDM + 25% | 38.2 | 7.5 | 1.4 | 4.7 | 2.2 | 18.6 |
| | HLTM | 45.3 | 0.9 | 0.1 | 0.5 | 0.0 | 9.5 |
| | B.M. Culture Medium | P.I. Day 10 | GM I. Day 10 | Mac I. Day 10 | BFUE I. Day 10 | Mixed I. Day 10 | Cluster Day 10 |
| Deionized Albumin | Base | 7.3 | 1.0 | 0.0 | 0.9 | 0.0 | 138.7 |
| | + Intralipid | 9.4 | 0.8 | 0.1 | 0.5 | 0.0 | 94.0 |
| | + Ethanolamine | 8.6 | 2.2 | 0.3 | 0.7 | 0.0 | 292.4 |
| | + Intra./Ethan. | 10.3 | 12.1 | 10.5 | 2.5 | 0.0 | 1565.6 |
| Non-Deionized Albumin | Base | 6.5 | 2.0 | 0.5 | 6.0 | 0.0 | 221.0 |
| | + Intralipid | 7.6 | 3.3 | 0.8 | 8.5 | 0.1 | 311.6 |
| | + Ethanolamine | 4.8 | 0.2 | 0.1 | 0.8 | 0.0 | 91.2 |
| | + Intra./Ethan. | 7.6 | 0.4 | 0.1 | 2.1 | 0.0 | 76.0 |
| Serum Controls | IMDM + 25% | 17.5 | 1.0 | 0.5 | 11.5 | 0.8 | 455.0 |
| | HLTM | 22.6 | 5.5 | 1.7 | 41.3 | 0.7 | 949.2 |

TABLE 1-continued

|  | MEAN<br>Culture<br>Medium | P.I.<br>Day 10 | GM I.<br>Day 10 | Mac I.<br>Day 10 | BFUE I.<br>Day 10 | Mixed I.<br>Day 10 | Cluster<br>Day 10 |
|---|---|---|---|---|---|---|---|
| Deionized | Base | 9.7 | 1.0 | 0.4 | 2.9 | 0.0 | 52.3 |
| Albumin | + Intralipid | 18.4 | 1.8 | 0.4 | 3.2 | 0.0 | 40.4 |
|  | + Ethanolamine | 14.9 | 3.5 | 0.5 | 1.0 | 0.1 | 108.1 |
|  | + Intra./Ethan. | 14.8 | 6.2 | 1.6 | 1.3 | 0.2 | 542.5 |
| Non-Deionized | Base | 8.0 | 1.2 | 0.7 | 4.4 | 0.7 | 82.2 |
| Albumin | + Intralipid | 12.7 | 2.1 | 0.7 | 3.6 | 0.1 | 107.7 |
|  | + Ethanolamine | 9.1 | 1.0 | 0.7 | 3.3 | 0.8 | 34.5 |
|  | + Intra./Ethan. | 17.1 | 1.4 | 0.5 | 6.3 | 3.9 | 30.1 |
| Serum | IMDM + 25% | 23.4 | 4.8 | 0.7 | 10.2 | 1.7 | 164.6 |
| Controls | HLTM | 27.5 | 3.8 | 0.7 | 16.0 | 1.0 | 328.9 |

TABLE 2

Percent CFU and CE for Cells Cultured in 295

|  | P.B<br>Culture<br>Medium | % GM<br>Day 10 | % Mac<br>Day 10 | % BFUE<br>Day 10 | % Mix<br>Day 10 | % Clusters<br>Day 10 | % CE<br>Day 10 |
|---|---|---|---|---|---|---|---|
| Deionized | Base | 11 | 0 | 80 | 0 | 10 | 1.3 |
| Albumin | + Intralipid | 21 | 0 | 70 | 0 | 9 | 1.6 |
|  | + Ethanolamine | 27 | 0 | 30 | 0 | 43 | 0.3 |
|  | + Intra./Ethan. | 48 | 3 | 23 | 0 | 26 | 0.3 |
| Non-Deionized | Base | 10 | 2 | 71 | 2 | 15 | 1.2 |
| Albumin | + Intralipid | 21 | 0 | 71 | 0 | 8 | 0.4 |
|  | + Ethanolamine | 12 | 1 | 81 | 2 | 3 | 2.4 |
|  | + Intra./Ethan. | 10 | 1 | 79 | 7 | 4 | 3.4 |
| Serum | IMDM + 25% | 19 | 2 | 72 | 1 | 6 | 2.3 |
| Controls | HLTM | 28 | 2 | 53 | 2 | 15 | 1.3 |

|  | P.B<br>Culture<br>Medium | % GM<br>Day 10 | % Mac<br>Day 10 | % BFUE<br>Day 10 | % Mix<br>Day 10 | % Clusters<br>Day 10 | % CE<br>Day 10 |
|---|---|---|---|---|---|---|---|
| Deionized | Base | 30 | 0 | 46 | 0 | 25 | 1.2 |
| Albumin | + Intralipid | 17 | 6 | 40 | 1 | 36 | 0.7 |
|  | + Ethanolamine | 51 | 4 | 24 | 2 | 18 | 4.2 |
|  | + Intra./Ethan. | 30 | 10 | 13 | 3 | 44 | 5.4 |
| Non-Deionized | Base | 28 | 9 | 38 | 2 | 23 | 0.7 |
| Albumin | + Intralipid | 36 | 3 | 38 | 3 | 20 | 2.1 |
|  | + Ethanolamine | 23 | 3 | 43 | 3 | 29 | 1.6 |
|  | + Intra./Ethan. | 43 | 0 | 36 | 0 | 21 | 0.3 |
| Serum | IMDM + 25% | 33 | 5 | 44 | 7 | 12 | 4.4 |
| Controls | HLTM | 26 | 2 | 30 | 0 | 42 | 0.5 |

|  | B.M.<br>Culture<br>Medium | % GM<br>Day 10 | % Mac<br>Day 10 | % BFUE<br>Day 10 | % Mix<br>Day 10 | % Clusters<br>Day 10 | % CE<br>Day 10 |
|---|---|---|---|---|---|---|---|
| Deionized | Base | 33 | 0 | 21 | 0 | 45 | 0.4 |
| Albumin | + Intralipid | 38 | 4 | 17 | 0 | 42 | 0.2 |
|  | + Ethanolamine | 38 | 3 | 0 | 0 | 50 | 0.7 |
|  | + Intra./Ethan. | 34 | 19 | 5 | 0 | 42 | 3.6 |
| Non-Deionized | Base | 23 | 4 | 48 | 0 | 25 | 1.4 |
| Albumin | + Intralipid | 26 | 4 | 45 | 1 | 24 | 1.7 |
|  | + Ethanolamine | 14 | 3 | 31 | 0 | 53 | 0.4 |
|  | + Intra./Ethan. | 14 | 3 | 54 | 0 | 29 | 0.4 |
| Serum | IMDM + 25% | 7 | 2 | 55 | 4 | 31 | 0.8 |
| Controls | HLTM | 12 | 2 | 63 | 1 | 21 | 2.0 |

|  | MEAN<br>Culture<br>Medium | % GM<br>Day 10 | % Mac<br>Day 10 | % BFUE<br>Day 10 | % Mix<br>Day 10 | % Clusters<br>Day 10 | % CE<br>Day 10 |
|---|---|---|---|---|---|---|---|
| Deionized | Base | 24 | 0 | 49 | 0 | 27 | 1.0 |
| Albumin | + Intralipid | 25 | 3 | 42 | 0 | 29 | 0.0 |
|  | + Ethanolamine | 39 | 2 | 21 | 1 | 37 | 1.7 |
|  | + Intra./Ethan. | 37 | 11 | 14 | 1 | 37 | 3.1 |
| Non-Deionized | Base | 20 | 5 | 53 | 1 | 21 | 1.1 |
| Albumin | + Intralipid | 28 | 2 | 51 | 1 | 17 | 14 |
|  | + Ethanolamine | 16 | 2 | 51 | 2 | 28 | 1.5 |
|  | + Intra./Ethan. | 22 | 1 | 56 | 2 | 18 | 1.4 |

TABLE 2-continued

Percent CFU and CE for Cells Cultured in 295

| Serum | IMDM + 25% | 20 | 3 | 57 | 4 | 16 | 2.5 |
|---|---|---|---|---|---|---|---|
| Controls | HLTM | 22 | 2 | 49 | 1 | 26 | 1.3 |

TABLE 3

| Culture Medium | P.I. | GM I. | Mac I. | BFUe I. | Mix I. | Clu I. |
|---|---|---|---|---|---|---|
| 295-1 + lipid 1 | 52 | 8 | 5 | 1 | 2 | 522 |
| control + serum | 40 | 8 | 27 | 3 | 24 | 386 |
| control − serum | 20 | 1 | 1 | 1 | 1 | 49 |

(Mean of 4–10 cultures from bone marrow and peripheral blood.)

TABLE 4

Colony Forming Units per 10,000 Cells Plated From Cells Cultured In 295

|  | GM | Mac | BFUE | Cluster | Total CFU | % GM | % Mac | % Clusters | % CE |
|---|---|---|---|---|---|---|---|---|---|
| RT2446-PB | | | | | | | | | |
| 295 | 2 | 20 | 30 | 94 | 146 | 1 | 14 | 64 | 1.5 |
| 295 + Lipid 3 | 4 | 2 | 10 | 70 | 86 | 5 | 2 | 81 | 0.9 |
| HLTM | 4 | 4 | 10 | 120 | 138 | 3 | 3 | 87 | 1.4 |
| RT2448-PB | | | | | | | | | |
| 295 | 14 | 22 | 29 | 88 | 153 | 9 | 14 | 58 | 1.5 |
| 295 + Lipid 3 | 5 | 8 | 15 | 34 | 62 | 8 | 13 | 55 | 0.6 |
| HLTM | 17 | 83 | 7 | 55 | 162 | 10 | 51 | 34 | 1.6 |
| UC1107-BM | | | | | | | | | |
| 295 | 0 | 0 | 0 | 0 | 0 | 0 | 0 | 0 | 0 |
| 295 + Lipid 1 | 22 | 25 | 19 | 79 | 145 | 15 | 17 | 54 | 1.5 |
| HLTM | 6 | 30 | 1 | 84 | 121 | 5 | 25 | 69 | 1.2 |
| ALLO-BM | | | | | | | | | |
| 295 | 4 | 5 | 16 | 32 | 57 | 7 | 9 | 56 | 0.6 |
| 295 + Lipid 1 | 6 | 3 | 2 | 30 | 41 | 15 | 7 | 73 | 0.4 |
| HLTM | 2 | 14 | 0 | 73 | 89 | 2 | 16 | 82 | 0.9 |
| RT2613-PB | | | | | | | | | |
| 295 | 14 | 2 | 20 | 30 | 66 | 21 | 3 | 45 | 0.7 |
| 295 + Lipid 2 | 10 | 0 | 30 | 74 | 114 | 9 | 0 | 65 | 1.1 |
| HLTM | 6 | 12 | 8 | 164 | 190 | 3 | 6 | 86 | 1.9 |
| RT2618-PB | | | | | | | | | |
| 295 | 0 | 0 | 24 | 16 | 40 | 0 | 0 | 49 | 0.4 |
| 295 + Lipid 2 | 8 | 0 | 42 | 66 | 116 | 7 | 0 | 57 | 1.2 |
| HLTM | 10 | 2 | 14 | 34 | 60 | 17 | 3 | 57 | 0.6 |
| RP7-BM | | | | | | | | | |
| 295 + Lipid 1 | 42 | 66 | 4 | 101 | 213 | 20 | 31 | 47 | 2.1 |
| 295 + Lipid 2 | 44 | 33 | 2 | 113 | 192 | 23 | 17 | 59 | 1.9 |
| HLTM | 69 | 59 | 4 | 178 | 310 | 22 | 19 | 57 | 3.1 |
| RP8-BM | | | | | | | | | |
| 295 + Lipid 1 | 30 | 30 | 3 | 91 | 154 | 19 | 19 | 59 | 1.5 |
| 295 + Lipid 2 | 55 | 44 | 13 | 136 | 248 | 22 | 18 | 55 | 2.5 |
| HLTM | 69 | 40 | 7 | 170 | 286 | 24 | 14 | 59 | 2.9 |

% CE = Total CFU/Total Cells Plated
Lipid 1 = Excyte
Lipid 2 = Nutrimax
Lipid 3 = Intralipid
BM = Bone Marrow
PB = Peripheral Blood The proliferation index for all cells at day 10 of culture ranged from 10–60 fold.

Generally, the number of CFU-GM in day 10 cultures increased 5–20 fold over day 0. The number of CFU-Mac in day 10 cultures increased 2–10 fold over day 0. Notably, the number of cluster forming units in day 10 serum-free cultures increased 10–600 fold over day 0.

At day 14 of the methylcellulose assay, GM colonies comprised about 10–50% of total colonies/clusters, Mac colonies comprised about 5–20% of total colonies/clusters, and clusters comprised about 10–60% of total colonies/clusters.

Typically, the percentage of colony-forming units (CFU) plus cluster-forming units (clFU) in 10-day serum-free cultures was relatively low, ranging from about 1 to 5% of the total cells (%CE=%cloning efficiency=total colonies+total clusters (x100)/total cells plated). However, the percentage of clFU within the total CFU/clFU was relatively high, ranging from about 10% to 50% of the total CFU/clFU. The absolute number of cluster-forming units per 10,000 cells ranged from 16 to 136. Cluster-forming units are the individual cells which proliferate directly into more mature forms of myelocytes such as band forms and segmented neutrophils.

EXAMPLE 7

Assessment of megakaryocyte precursors grown in serum-free medium

Figure 7:
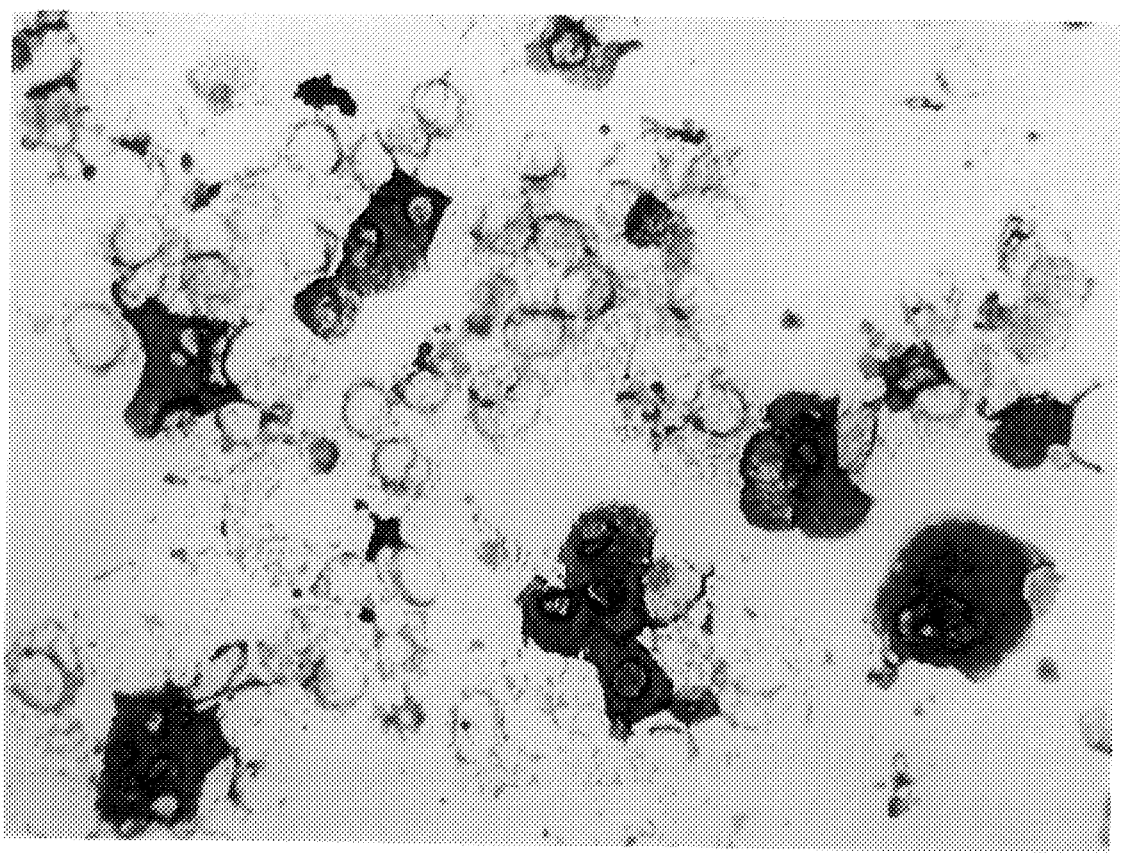
FIG. 7 shows megakaryocyte precursors labeled by immunocytochemistry (red) in a field of myelocytic cells (blue).

Cells were grown in culture as described in Example 4, with serum-free medium formulation 295-1 as described in Example 1. At selected days of culture, cells were cytocentrifuged onto microscopic slides, fixed with absolute acetone, and incubated with an anti-CD41a monoclonal antibody designated P2 (AMAC, Westbrook, Me.). The antibody recognizes platelet/megakaryocyte specific glycoprotein IIb/IIIa. Glycoprotein IIb/IIIa is present in megakaryocyte precursors, mature megakaryocytes, and platelets, but not in other blood cells. After incubation with the primary antibody, a secondary antibody (biotinylated goat anti-mouse IgG, Kirkegaard & Perry, Gaithersburg, Md.) was added and bound to the primary antibody. This was followed by incubation with a streptavidin-peroxidase complex and a peroxidase (AEC) reaction, which produced a red color specifically labeling megakaryocytes, their precursors and their descendents. The cultures were then counterstained with hematoxylin, which produced a blue color on cell nuclei, allowing recognition of negative cells (see FIG. 7).

Cells from the same cultures were also analyzed by flow cytometry to detect anti-CD41a labeled cells. Results are shown in Tables 5–7 below.

TABLE 5

Immunocytochemistry and Flow Cytometry Evaluation of MK Cells

| Culture | 295 +~ | Time (day) | CD41a Immu (%) PL-STK | MK | CD41a Flow (%) MK | % mFSC | % hFSC |
|---|---|---|---|---|---|---|---|
| PB CD34 | GF(1) | 7 | 8 | 12 | 17.8 | 83.1 | 17.4 |
| PB CD34 | GF(2) | 7 | 7 | 18 | 17.4 | 82.8 | 16.7 |
| PB CD34 | GF(2) | 7 | 7 | 19 | 17.5 | 81.7 | 18.9 |
| PB CD34 | GF(2) | 7 | 19 | 25 | 16.5 | 81.8 | 18.2 |
| PB CD34 | GF(2) | 7 | 8 | 20 | 15.3 | 83.7 | 16.4 |
| PB CD34 | GF(2) | 8 | 1 | 7 | 2.6 | 84.6 | 15.4 |
| PB CD34 | GF(2) | 8 | 0 | 6 | 3.3 | 89.9 | 12.1 |
| PB CD34 | GF(1) | 8 | 0 | 4 | 3.0 | 90.0 | 10.0 |
| | Mean | | 6.3 | 13.9 | 11.7 | 84.7 | 15.6 |
| | SEM | | 2.2 | 2.7 | 2.6 | 1.2 | 1.1 |

TABLE 5-continued

Immunocytochemistry and Flow Cytometry Evaluation of MK Cells

| Culture | 295 +~ | Time (day) | CD41a Immu (%) PL-STK | MK | CD41a Flow (%) MK | % mFSC | % hFSC |
|---|---|---|---|---|---|---|---|
| PB CD34 | GF(1) | 10 | 0 | 23 | 20.0 | 77.0 | 23.5 |
| PB CD34 | GF(2) | 10 | 0 | 19 | 20.7 | 73.4 | 26.6 |
| PB CD34 | GF(2) | 10 | 0 | 29 | 19.8 | 73.2 | 26.8 |
| PB CD34 | GF(2) | 10 | 0 | 33 | 21.3 | 76.1 | 23.9 |
| PB CD34 | GF(2) | 10 | 0 | 23 | 19.6 | 71.9 | 28.6 |
| PB CD34 | GF(2) | 10 | 0 | 22 | 20.7 | 80.2 | 20.3 |
| PB CD34 | GF(1) | 10 | 0 | 6 | 6.7 | 77.6 | 22.4 |
| PB CD34 | GF(2) | 10 | 0 | 7 | 5.2 | 93.4 | 10.5 |
| PB CD34 | GF(1) | 10 | 1 | 8 | 4.5 | 86.7 | 13.3 |
| | Mean | | 0.1 | 18.9 | 15.3 | 78.5* | 21.8# |
| | SEM | | 0.1 | 3.3 | 2.6 | 2.1 | 2.1 |

Key: Immu, immunocytochemistry; flow, flow cytometry; PL-STK, platelet stuck, CD41a-negative cells; MK, megakaryocytic, CD41a-positive cells; % mFSC, % medium forward scatter, smaller cells in the MK population; % hFSC, % high forward scatter, larger cells in the MK population.
*significantly lower than mFSC at 7–8 days.
significantly higher than hFSC at 7–8 days.
Growth factors: (1) SCF, IL-3, and IL-6; (2) SCF, IL-3, IL-6, and IL-11.

TABLE 6

Evaluation of Megakaryocytes in BM Samples

| Sample | Wright's MK Morph | Immunocyto-chemistry CD41a* | CD42b* | Flow Cytometry CD41a | CD42b | CD61 |
|---|---|---|---|---|---|---|
| Fresh Samples: | | | | | | |
| BM MNC1 | 0.05 | 0.4 (32) | ND | 23.3 | 16.7 | 22.1 |
| BM MNC2 | 0.01 | 0.5 (39) | ND | 27.3 | 5.5 | 9.5 |
| BM MNC3 | 0.01 | 0.2 (45) | 0.5 (0) | 9.5 | 4.2 | 6.5 |
| BM CD34+ | 0.00# | 9.0 (35) | ND | 40.0 | ND | ND |
| Cultured Samples (day 10–14): | | | | | | |
| BM MNC | 2.7 | 14.7 (0) | 4 (0) | 15.6 | 3.7 | ND |
| BM Madroph | 0 | 0 (0) | 0 (0) | 0.02 | 0 | 0 |

Frequencies (%) of indicated cells are presented in the table. Abbreviations: BM Macroph, bone marrow macrophages (98% of the cells in this culture were morphologically macrophages); ND, not done.
*Numbers in the parenthesis represented frequencies (%) of platelet-stuck, CD41a⁻ or CD42b⁻ cells.
Morphologically CD34+ cells were lymphocyte- or blast cell- like.

TABLE 7

DIBTRIBUTION OF MEGAKARYOCYTE IN DIFFERENT CULTURES

| Sample | Coniditions | Time (Day) | CD41a+ (%) | Cell ($10^5$/ml) |
|---|---|---|---|---|
| BM MNC | HLTM+ (1)* | 7 | 2 (0)# | 7.4 |
| | HLTM+ (1) | 10 | 4 (0) | 9.4 |
| | Plasma+ (1) | 12 | 14.7 (2) | 13.0 |
| RT 555 (3/23/93) | 295+ (2)* | 12 | 10 (2) | 3.2 |
| | HLTM+ (2) | 12 | 3 (1) | 5.8 |
| UC 166 | 295+ (2) | 14 | 11 (9) | 17.3 |

TABLE 7-continued

DIBTRIBUTION OF MEGAKARYOCYTE IN DIFFERENT CULTURES

| Sample | Coniditions | Time (Day) | CD41a+ (%) | Cell (10⁵/ml) |
|---|---|---|---|---|
| (3/17/93) | HLTM+ (2) | 14 | 0.5 (1) | 8.4 |
| GB (2/1/93) | HLTM+ (2) | 13 | 0 (0) | — |

*Cytokine combination (1): SCF, IL-3 & IL-6. Cytokine combination (2): SCF, IL-3, GM-CSF & G-CSF.
Numbers in ( ) represent platelet-stuck cells (false positive).

Platelets stained positive with anti-CD41a, CD41b (GP Ib) and CD61 (GP IIIa) were often observed to adhere to other cells not of megakaryocyte lineage. It was found that flow cytometry, as shown in Table 6, was subject to the artifact of platelet-adherence by counting false positive cells. Therefore, CD41a immunocytochemistry using the same monoclonal antibody was utilized to confirm the true megakaryocyte lineage cells. As shown in Table 5, most of the adherent platelets ("PL-STK") disappeared after 7–10 days in culture, and comparable results were obtained from immunocytochemistry and flow cytometry.

Figure 8A:
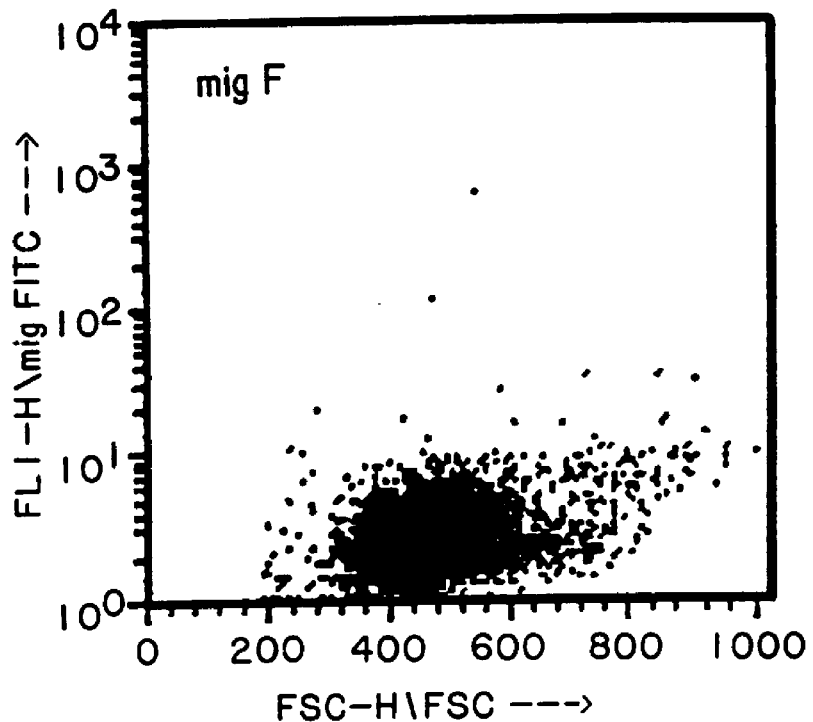
Figure 8B:
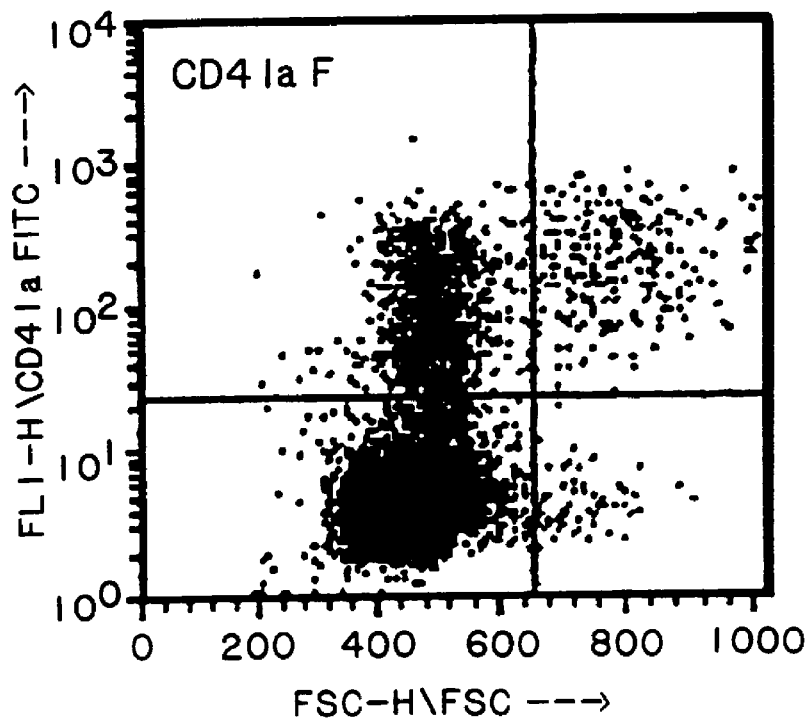

Using flow cytometry, the expression of CD41a antigen and the cell size were simultaneously analyzed. FIG. 8 shows the flow cytometric dot-plot of a culture sample which was grown in the serum-free medium for 10 days. The X axis represents the forward light scatter (FSC) which measures the cell size. Those cells which plotted further to the right are higher in FSC (hFSC) and larger in cell size. The Y axis represent the green fluorescence intensity which measures the FITC conjugated antibody staining. The isotype control staining of the sample using FITC conjugated anti-mouse IgG is presented in FIG. 8a, showing no non-specific antibody binding to the cells. The same cell sample incubated with FITC conjugated anti-CD41a antibody is presented in FIG. 8b, showing distinctively CD41a positive megakaryocytes in the culture. The cells plotted in the upper right quadrant are considered large megakaryocytes and their cell size is larger than that of the majority of the cell population in the sample. Those cells plotted in the upper left quadrant are considered small megakaryocytes. It has been reported that large megakaryocytes are more mature than small megakaryocytes (Tomer, A, et al., Blood 70:1635–1742, 1987). As shown in Table 5, large megakaryocytes (hFSC) comprised about 16% of the total labelled cell population in day 7–8 cultures. After 10 days of culture, the frequency of large megakaryocytes had progressed to about 22%, demonstrating a statistically significant increase in megaryocyte maturation.

As shown in Table 7, when grown in serum-free medium (295), hemopoietic cells from the same donor yield more megakaryocytes (3–22 fold) than when grown in the serum-containing medium (HLTM). The results strongly suggest that the serum-free culture medium provides a more favorable microenvironment for megakaryocyte growth than does the serum-containing medium.

EXAMPLE 8

Megakaryocyte colony formation analyzed by fibrin clot assay

At selected days in culture, cells were plated in a serum-free fibrin-clot colony culture (MK-CFC assay) and evaluated for their ability to form megakaryocyte colonies. Cells ($2 \times 10^5$/ml) were suspended in a semisolid fibrin-clot culture medium containing 1% BSA (Sigma), 0.02 % fibrinogen (KABI, Sweden) and 0.02 U/ml thrombin (Sigma) in IMDM (Zauli, G, et al., Exp Hematol 20:850–854, 1992). Cytokines including SCF, IL-3, IL-6, and/or IL-11 were also utilized as indicated. A 0.5 ml sample of the cell/medium suspension was placed on an ordinary microscope slide. The slide was placed in a humidified 150 mm Petri dish and cultured at 37° C., 5% $CO_2$ for 14 days. During this time, megakaryocyte precursors in the original culture proliferated to form megakaryocyte bursts and colonies, or differentiated into more mature single megakaryocytes. The fibrin-clot cultures were then fixed and immunostained as described in Example 7.

The above described MK-CFC assay offers several improvements and advantages over previously described assays. Firstly, the Petri dish has been replaced by the microscope slide as a substrate for the megakaryocyte colony cultures, which offers these advantages:

(1) The slide enables the use of absolute acetone, the best fixative to preserve the protein antigen for the immunocytochemical detection. Traditionally, the colony cultures were grown in plastic Petri dishes, which would dissolve in acetone.

(2) The slide facilitates the immunostaining by decreasing the amount of antibody used for each culture and diminishing the artifact caused by antibody dry out during staining.

(3) The slide permits clear examination of the in situ colonies by using high power microscopic objectives.

The traditional evaluation methods included morphological recognition wherein megakaryocyte colonies were described as clusters of big, highly refractile cells under the inverted microscope without any staining (Sonoda, Y., et al., Blood 81:624–630, 1993) and immunfluorescent microscopy where megakaryocyte colonies were distinguished from other colonies as bright green vs. dull green (background) (Bruno, E., et al., Blood 73:671–677, 1989; Zauli, G., et al., Exp. Hematol. 20:850–854, 1992). These methods yielded ambiguous results because it was difficult to distinguish between true megakaryocyte colonies and non-megakaryocyte lineage colonies, which also grow in fibrin clots.

Figure 9:
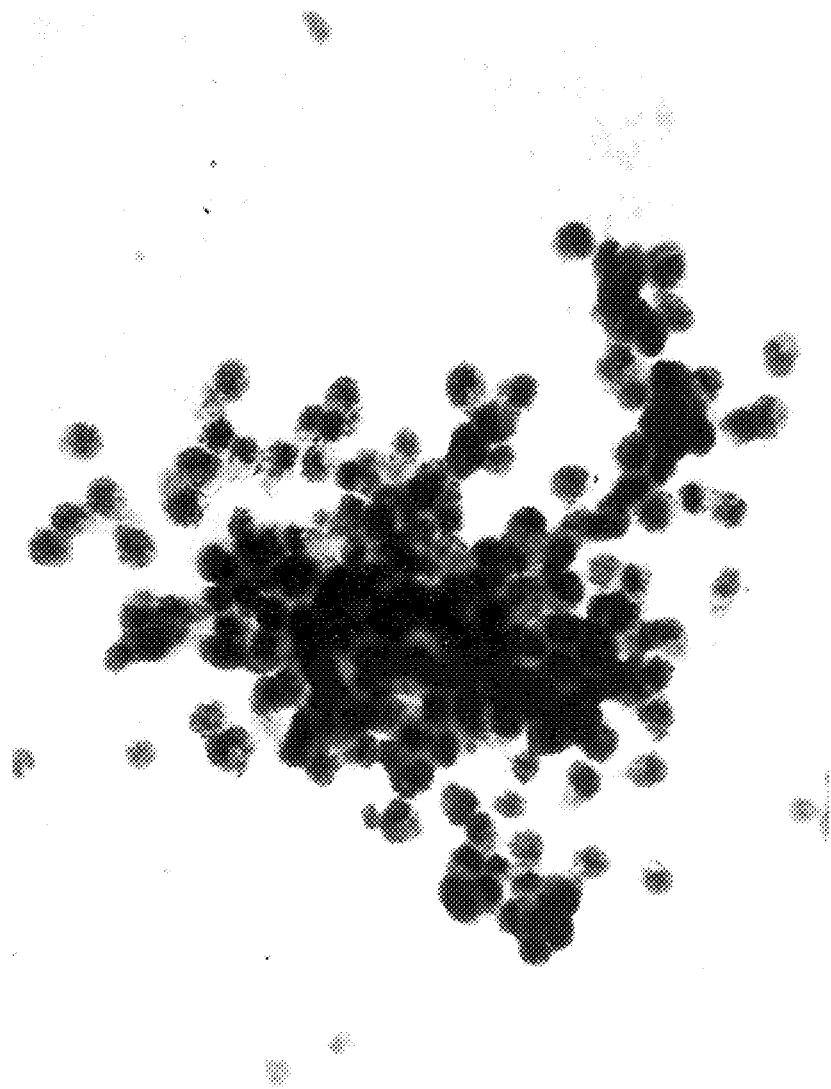
FIG. 9 shows a typical megakaryocyte burst developed in a fibrin clot assay.

The present method provides more accurate counting of megakaryocyte colonies because they are identified by a specific red label, within blue-labelled non-megakaryocytes, under the light microscope (FIG. 9). Results are summarized in Table 8 below.

TABLE 8

EFFECTS OF CULTURE MEDIA AND CYTOKINES ON MEGAKARYOCYTE LINEAGE DEVELOPMENT
(Serum-Free Fibrin-Clot Assay)

| Sample | Pre-Cul Time (days) | Pre-Cul Cond & Cytokine* | MK Lineage Cells per 10⁵ Cells | | |
|---|---|---|---|---|---|
| | | | BFU-MK | CFC-MK | S-MK |
| Exp 1 | 5 | HLTM+ (1) | 0 | 1.9 | 13.5 |
| | 5 | 295+ (1) | 0 | 0 | 2.65 |
| | 5 | 295+ (2) | 40 | 30 | 335 |
| | 12 | HLTM+ (1) | 0 | 25.9 | 98.2 |
| | 12 | 295+ (1) | 0 | 32.2 | 652.4 |
| | 12 | 295+ (2) | 0 | 66 | 641.5 |
| Exp 2 | 7 | 295+ (1) | 0 | 19.6 ± 9.7 | 134.4 ± 71.9 |
| | 7 | 295+ (2) | 43.7 ± 9.4 | 104.3 ± 14.2 | 15.0 ± 5.8 |
| | 7 | 295+ (3) | 7 | 36.5 | 7.5 |

PB CD34+ cells were grown in the pre-cultured conditions for the indicated times and then plated into fibrin-clot cultures for a 14-day of further growing. Abbrevs: Cul, culture, Cond, conditions; MK, megakaryocyte; BFU-MK, megakaryocyte burst-forming cell, the colony containing 40–100 megakaryocytes; CFC-MK, megakaryocyte colony-forming cell, the colony containing 2–39 megakaryocytes; S-MK, single megakaryocyte found in the colony culture.
*Cytokine combinations: (1) stem cell factor, IL-3 & IL-6; (2) stem cell factor, IL-3 & GM-CSF; (3) stem cell factor, IL-3, CM-CSF & IL-11.

As shown in Table 8, the early megakaryocyte progenitors (BFU-MK) were detectable only in the serum-free (295) but not the serum-containing (HLTM) cultures during days 5–7. On day 12, serum-free cultures contained more megakaryocyte colony forming cells (MK-CFC) and single megakaryocytes (S-MK) than serum-containing cultures. The addition of GM-CSF into the serum-free culture appeared to facilitate the growth of megakaryocytes.

EXAMPLE 9

DIFFERENTIATION OF MEGAKARYOCYTES IN SERUM-FREE MEDIUM

This example further assesses the growth and differentiation of CD34$^+$ cell cultures into megakaryocytes in serum-free media compared to serum containing media. The effects of different combinations of growth factors on megakaryocyte differentiation was also determined.

The isolation and culture of CD34$^+$ hematopoietic cells from bone marrow (BM) and peripheral blood (PB) was performed by methods similar to those described in Examples 1 through 3. Briefly, apheresis products of PB cells and plasma were simultaneously collected using a CS3000™ blood cell separator (Fenwal Division, Baxter Healthcare, Deerfield, Ill.) from cancer patients 4–15 days after G-CSF and/or chemotherapy mobilization. Cell samples were collected in citrate dextrose formula A (ACDS) and diluted 1:1 with Iscove's modified Dulbecco's medium (IMDM) (Gibco, Grand Island, N.Y.) containing 2% fetal bovine serum (FBS) (Sigma, St. Louis, Mo.). Low-density MNC were obtained after density centrifugation over Histopaque™ ficoll-hypaque (1.077 g/ml) for 20 min at 300 g. The plasma was spun for 10 min at 200g to remove platelets, passed through a 0.45 μm filter and stored at −20° C. Human aplastic serum was obtained from thrombocytopenic patients after BM transplantation as described by Debili et al. (*Blood* 80:3022 (1992)). Aplastic serum and plasma (AS) that demonstrated megakaryocyte stimulatory activities in pre-screened studies were utilized in these experiments at a final concentration of about 10%.

CD34 positive cells were selected as previously described in Example 2 with slight modifications. Briefly, adherent cells were depleted by mixing the MNC with uncoated polystyrene Dynal paramagnetic beads (Fenwal Division, Baxter Healthcare, Deerfield, Ill.). Non-adherent cells were incubated with the anti-CD34 monoclonal antibody (mAB) 9C5 (Immunotherapy Division, Baxter Healthcare, Santa Ana, Calif.) and then mixed with magnetic beads coated with sheep anti-mouse IgG$_1$ (Fenwal Division, Baxter Healthcare, Deerfield, Ill.) at the ratio of 0.5–1 bead to 1 cell. Bead-cell rosettes were collected after the positive selection using a Dynal MPC-1 Magnet (Immunotherapy Division, Baxter Healthcare, Santa Ana, Calif.) or Isolex™ 50 magnetic cell separator (Immunotherapy Division, Baxter Healthcare, Santa Ana, Calif.). Cells were released from beads by overnight incubation with 200 U/ml IL-3 at 37° C., 5% CO$_2$. For quantitation aliquots of selected cells were stained with another mAB against CD34, fluorescein (FITC) conjugated 8G12 (Immunotherapy Division, Baxter Healthcare, Santa Ana, Calif.). Flow cytometry demonstrated that about 80–97% of the selected cells were CD34 positive.

BM mononuclear cell (MNC) cultures were initiated at 10$^5$ cells/ml while CD34 cell cultures were initiated at 10$^4$ cells/ml. Cultures were grown in the human long term culture medium (HLTM), the serum-free medium (Immunotherapy Division, Baxter Healthcare) or the human serum or plasma-supplemented medium. Immunocytochemistry and flow cytometry was performed as described in Example 7.

Figure 10:
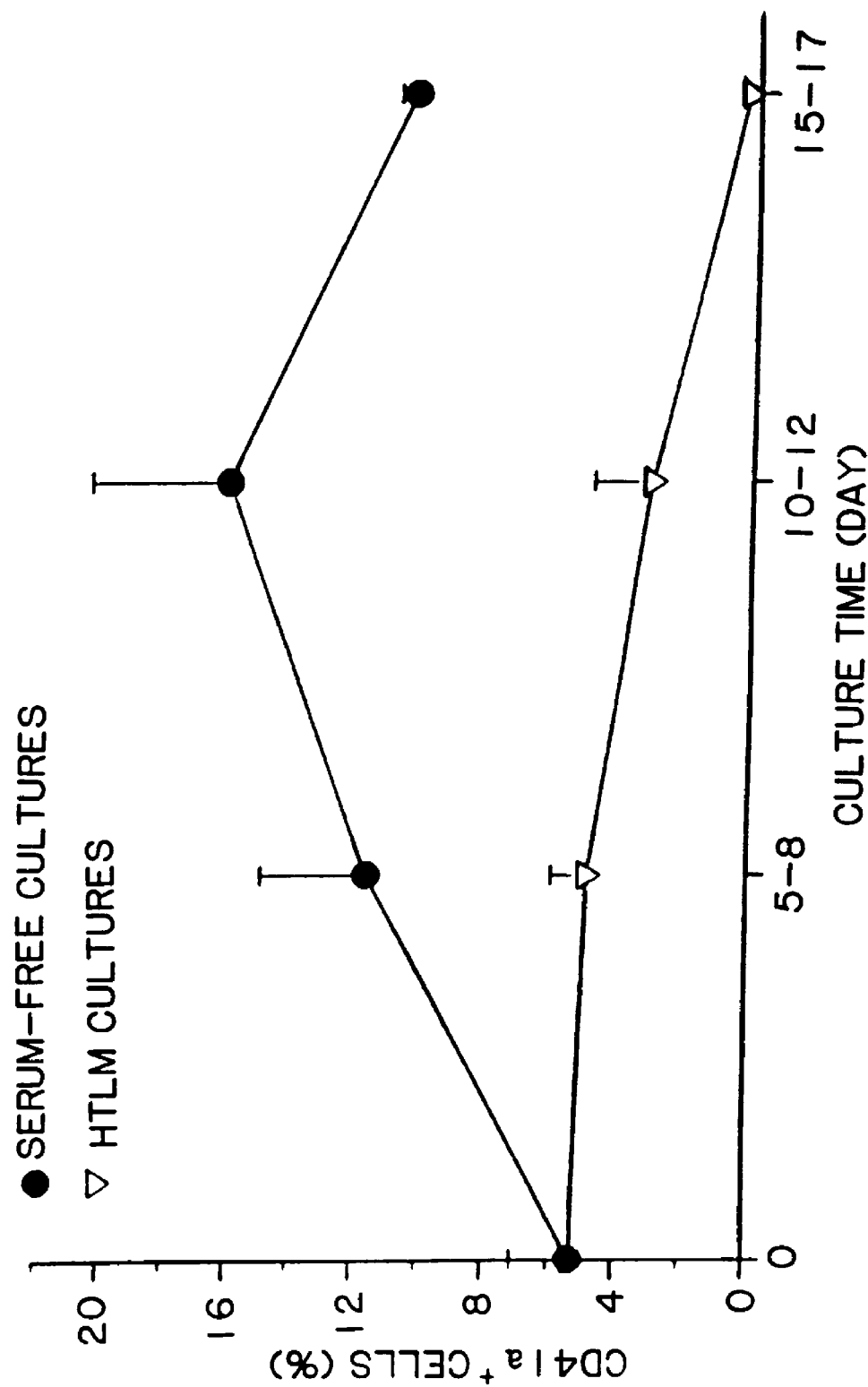
FIG. 10 shows the kinetics of megakaryocyte cell growth in serum-free cultures compared to normal media.

The kinetics of megakaryocyte growth in culture was determined in serum-free and HLTM cultures supplemented with SCF, IL-3 and IL-6. Immunocytochemistry showed that, prior to culture on day 0, CD41a$^+$ cells represented 0.03% (ranged 0.01–0.05%, n=5) of unselected BM MNC and 5.3% (ranged 2–9 %, n=5) of purified BM CD34$^+$ or PB CD34$^+$ cells (FIG. 10, day 0). No obvious cell proliferation was observed during the first several days after plating. In order to maintain cultures for later evaluation, cells were not harvested until day 5. Cultures were grown for a period of 10–30 days. Some stromal foci were occasionally formed in HLTM BM CD34 cell or MNC cultures. Serum-free cultures had a few scattered, macrophage like adherent cells but no stromal foci.

On day 5, all CD34 cell cultures increased 4–5 fold in cellularity, with viable cells greater than 95%. The differential cell count showed that day 5 serum-free CD34$^+$ cell cultures contained 66.2% blast cells (ranged 40–98%) and 37% granulocytic lineage cells (ranged 9–53%). At day 10–12, serum-free CD34 cell cultures contained 21.3 ±6.5% blast cells (ranged 9–47%), 70.3±6.7% granulocytic cells (ranged 42–88%), 8.2±1.8% macrophages (ranged 2–14%) and occasionally erythroid cells (5%). HLTM CD34 cell cultures generally contained less blast cells (9.2±3.2%, ranged 1–22%) and more granulocytic cells (78.2±5.3%, ranged 65–96%). Cell viability and proliferation were slightly higher in HLTM cultures than in serum-free culture. Morphologically recognizable mature megakaryocytes were found in HLTM cultures but not in serum-free cultures. As compared to mature megakaryocytes present in BM, culture-derived, morphologically recognizable megakaryocyte had a smaller cell size and less lobulated nuclei (2–3 lobes).

TABLE 9

MEGAKARYOCYTE GROWTH IN CD34+ CELL CULTURES

| CULTURE | CD41a$^+$ (%) | VIABLE (%) | TOTAL CELL INCREASE (fold increase) | MEGA-KARYO-CYTE fold increase** |
|---|---|---|---|---|
| Serum-Free | 16.2 ± 4.3* | 75.9 ± 1.0 | 22.0 ± 6.0 | 51.0 ± 3.8* |
| HLTM | 3.1 ± 1.8 | 83.4 ± 2.1 | 29.1 ± 9.2 | 14.1 ± 2.2 |

PB CD34$^+$ cell cultures were grown in HLTM (n = 6) or serum-free media (n = 7) supplemented with SCF, IL-3 & IL-6 for 10–14 days prior to examination.
**estimated fold expansion of megakaryocyte, where the initial cell populations was estimated to contain 53 ± 1.8% CD41a$^+$ megakaryocyte.
*Significantly higher than that in HLTM.

Distinctive CD41a$^+$ cells were observed in day 10–14 in serum-free CD34 cultures (FIG. 9). Under serum-free conditions, the percent of CD41a$^+$ megakaryocyte progenitors was substantially higher than that observed under serum containing conditions. Similarly, the fold expansion of these cells as compared to the starting cell population was 51 fold in serum-free media versus 14.1 fold in serum containing media (Table 9). These cells showed cytoplasmic CD41a immunoreactivity, containing a single, non-lobulated nucleus and non-granular cytoplasm. Their size was similar or slightly bigger than the surrounding granulocytes. Without the antibody staining, they could not be recognized by light microscopy. These CD41a$^+$ megakaryocyte lineage cells increased around day 5–7 (1.4±3.1%) peaked at day 10–12 (16.2±4.3%) and decreased around day 15–17 (10.5±0.5%) in serum-free CD34 cell cultures (FIG. 10). HLTM cultures, however, showed no increase of megakaryocyte frequency throughout the entire culture period (FIG. 10); but absolute megakaryocyte number increased and peaked also at day 10–12, mainly due to the high cellularity and the moderate megakaryocyte frequency at that time. Morphologically recognizable megakaryocyte accounted for about ⅕ of total CD41a⁺ cells in day 10–12 HLTM cultures. Others were morphologically unrecognizable megakaryocyte similar to those found in serum-free cultures. Megakaryocytes disappeared from HLTM cultures around day 15. HLTM cultures progressed to day 30 did not regain megakaryocytes. Megakaryocyte derived from day 10–12 serum-free or HLTM cultures were brightly stained with CD41a and easily recognized by immunocytochemistry and flow cytometry.

Figure 11:
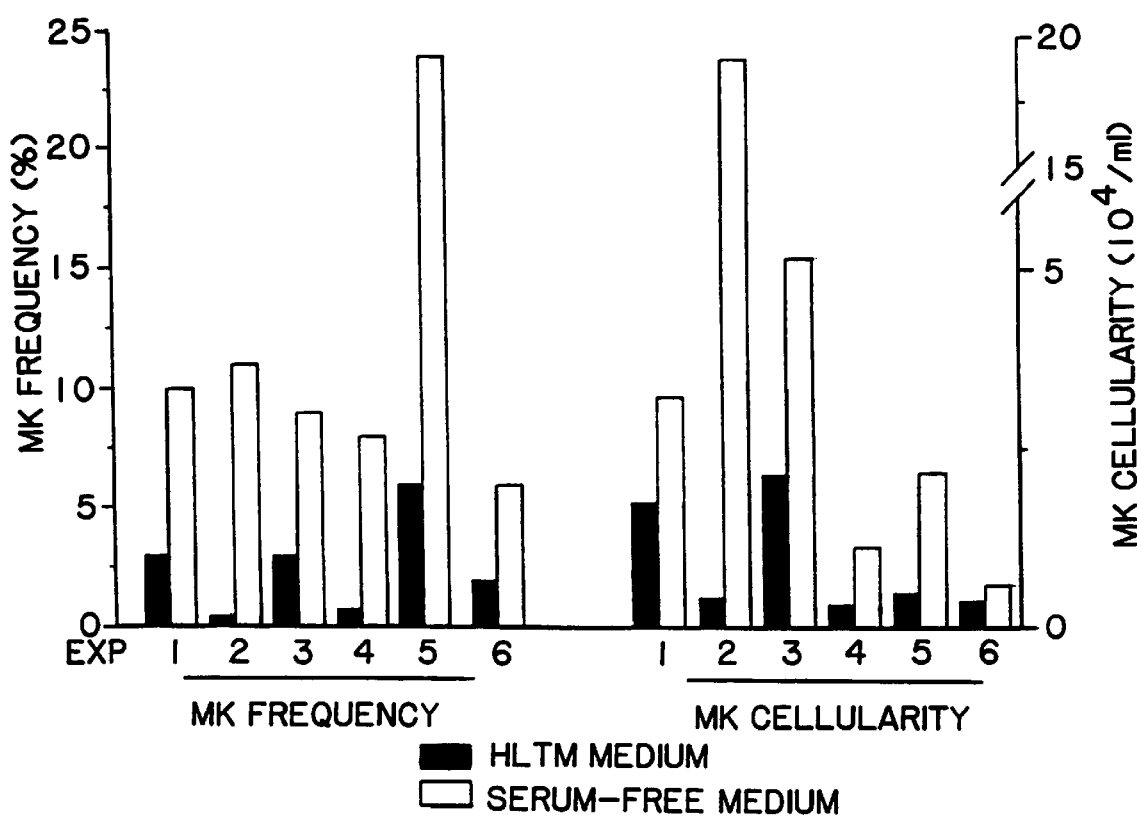
FIG. 11 shows the effects of serum-free culture media compared to normal media or megakaryocyte growth from isolated CD34+ cultures.

Paired PB CD34⁺ cell cultures were established to compare the ability of different culture media to support megakaryocyte growth. PB CD34⁺ cells from individual donors were grown in serum-free and HLTM cultures. Cultures were supplemented with the identical cytokine combination and refed with the same regimen. Results from 6 experiments are presented in FIG. 11. Experiments 1–3 were supplemented with SCF, IL-3, GM-CSF & G-CSF; while experiments 4–6 were supplemented with SCF, IL-3 & IL-6. Cell viability in paired cultures was similar. Cell count was generally lower in serum-free cultures than in HLTM cultures with the exception of experiment 2 (FIG. 11). Megakaryocyte frequency in serum-free cultures was 7.6±3.1 fold higher (ranged 3–22) than their paired HLTM cultures. The absolute megakaryocyte number in serum-free cultures was 17.4±7.1 fold higher (ranged 2–45) than their comparative HLTM cultures (FIG. 11, megakaryocyte cellularity).

In other independent experiments, in vitro total megakaryocyte expansion was calculated by dividing the estimated cultured megakaryocyte output by the initial megakaryocyte population, and standardized by the cultured cell viability. Megakaryocyte fold expansion was 51-fold in serum-free medium and 14-fold in HLTM cultures (Table 9). Therefore, the serum-free media supported better megakaryocyte growth than the HLTM medium, probably by facilitating megakaryocyte differentiation from CD34⁺ cells and Mk proliferation. Culture medium support of megakaryocyte growth from different cell groups including BM MNC, BM CD34⁺ and PB CD34⁺ cells were also investigated (FIG. 12). SCF, IL-3 & IL-6 were added to all cultures. As a positive control, IMDM BM MNC cultures were further supplemented with AS. HLTM cultures constantly yielded 2–3% megakaryocyte, no matter if they were derived from purified CD34⁺ cells or unpurified BM MNC. Serum-free cultures, except for BM MNC, yielded a higher percentage of megakaryocyte than HLTM cultures. In addition, serum-free PB CD34 cell cultures grew more megakaryocyte (16.1±4.3%) and expanded more (22.0±6.0 fold) than serum-free BM CD34 cell cultures (9.3±1.6% megakaryocyte, 8.9±1.3 fold expansion) (FIG. 12). Cell viability in both cultures was similar (80.0±6.0% vs. 86.3±1.3%). Therefore, the serum-free medium appeared to support megakaryocyte growth better in PB CD34 than in BM CD34 cell cultures, or there may have been more megakaryocyte precursors to begin with. On the other hand, the serum-free medium compared unfavorably with HLTM BM MNC cultures (FIG. 12). In addition, the cell count increased in HLTM BM MNC (4–10 fold) but not in serum-free BM MNC cultures. The growth of megakaryocytes from BM MNC appeared to depend on the presence of stromal foci, which were formed in IMDM (containing human AS) and HLTM (containing animal serum) but not in serum-free cultures. The addition of AS to the serum-free medium on day 0 rendered the medium supportive of megakaryocyte growth from BM MNC in both HLTM and IMDM media (FIG. 12).

To determine the effects of cytokines, paired PB CD34⁺ cell cultures were set up and assayed for their ability to support megakaryocyte growth. Results from a typical experiment are presented in FIG. 13. In HLTM cultures, the only effective cytokine combination was SCF+IL-3 +IL-6. In serum-free cultures, SCF+IL-6 or SCF+GM-CSF combinations supported baseline megakaryocyte growth. The addition of IL-3 to either of these combinations increased megakaryocyte proliferation (FIG. 13). GM-CSF stimulated more cell proliferation than IL-6 when combined with SCF & IL-3, without changing the megakaryocyte frequency. Serum-free cultures supplemented with GM-CSF+SCF+IL-3 thus contained higher total cell count and megakaryocyte number than cultures supplemented with IL-6+SCF+IL-3 (FIG. 13, megakaryocyte cellularity). The same was true when comparing serum-free cultures supplemented with SCF, IL-3, GM-CSF & G-CSF (Experiment 1–3 in FIG. 11) with those supplemented with SCF, IL-3 & IL-6 (Experiment 4–6 in FIG. 11). The addition of 200 U/ml IL-11 to the SCF+IL-3+GM-CSF combination did not stimulate further megakaryocyte proliferation (FIG. 13). To exclude the possibility of improper dosage, IL-11 was titrated at concentrations between 50 and 800 U/ml with the SCF+IL-3+IL-6 combination in PB CD34⁺ cell cultures. Although high dose IL-11 (400 Uml) might enhance cell proliferation, no obvious synergistic effects of IL-11 with this cytokine combination on megakaryocyte growth were observed.

As morphologically recognizable megakaryocyte were found in serum-containing but not in serum-free cultures, serum effects on megakaryocyte growth and morphology differentiation were evaluated. Human AS was added to cultures at different times. On day 0, paired BM CD34 cell cultures (n=3) were supplemented with AS alone, cytokines (SCF, IL-3 & IL-6) alone, or AS+cytokines. At day 10–12, AS-alone cultures showed a high megakaryocyte frequency (around 15%) but virtually no cell expansion (0.5–1 fold); while cytokines-alone and cytokines+AS cultures had a lower megakaryocyte frequency (around 8%) and a high cell expansion (around 20 fold and 38 fold, respectively). Morphologically recognizable megakaryocyte accounted for ⅓–½ and ⅐–⅓ of total CD41a⁺ cells in AS-alone cultures and AS+cytokine cultures, respectively. Virtually no cells with megakaryocyte morphology were found in cytokine-alone cultures. However, when these cytokine-alone cultures were added with AS at day 10–12, morphologically recognizable megakaryocyte emerged 3–4 days later and accounted for ⅕–⅓ of total CD41a⁺ cells. Megakaryocytes in control cultures (without AS addition) remained morphologically unrecognizable. BM MNC cultures initially depleted of megakaryocyte morphology and stimulated with As+cytokines yielded morphologically recognizable megakaryocytes (⅕–⅓ of total CD41a⁺ cells) after 10–12 days of culture. These results indicated that serum can be used to facilitate megakaryocyte morphology differentiation whereas serum-free conditions tend to maintain an immature phenotype.

The above results demonstrate that the serum-free medium is better than the serum-containing HLTM medium in support of megakaryocyte growth from purified CD34+ hemopoietic progenitors. PB CD34⁺ cells showed a higher megakaryocyte potential than BM CD34⁺ cells when they were grown in the serum-free medium. The majority of megakaryocyte derived from serum-free cultures expressed the GP IIb/IIIa antigen, and were morphologically unrecognizable as mature megakaryocytes. They could undergo further differentiation and acquired megakaryocyte morphology upon further stimulation by aplastic serum.

EXAMPLE 10

SERUM-FREE SUSPENSIONS OF HUMAN HEMATOPOIETIC CELLS

This example shows the preparation and growth of serum-free suspensions of human hematopoietic cells in media other than the 295-1 media described previously.

Apheresis blood products from breast cancer patients pre-treated with chemotherapy and G-CSF were obtained from the University of Chicago. The CD34$^+$ cells were selected from the apheresis blood products with the Isolex™ 50 (Baxter Healthcare, Corp., Fenwal Division) or the Isolex™ 300 (Baxter Healthcare, Corp., Immunotherapy Division, Irvine, Calif.) Magnetic Cell Separator. These systems are designed to select CD34$^+$ cells from apheresis blood using an anti-CD34 monoclonal antibody (9C5) and retrieval using Dynal IgG$_1$FC, ST magnetic beads. The 9C5 anti-CD34 monoclonal antibody was added to the apheresis blood product at 0.5 ug (stock vial at 1 ug/ul) per $1 \times 10^4$ cells in the Isolex™ 50 or Isolex™ 300 column. The cells were then rotated for 30 minutes on the Isolex™ rotator. The cells were washed twice, in order to remove the unbound 9C5 monoclonal antibody, in RPMI 1640 containing 1% human serum albumin (HSA). The cells were then diluted in the column to $1-2 \times 10^7$ cells/ml with RPMI 1640 containing 10 mg/ml (1%) HSA and 1 mg/ml (0.1%) Gammagard® (Baxter Healthcare Corp., Hyland Division, Glendale, Calif.). Dynal IgG$_1$FC, ST magnetic beads (Dynal, Oslo, Norway) were added to the cell suspension at 0.5 bead to cell ratio and rotated for 30 minutes on the Isolex™ rotator. The CD34 cell:bead complexes were then removed using a magnet.

The CD34$^+$ cell:bead complexes were resuspended to $3 \times 10^5$ cells/ml in X-VIVO 10 (BioWhittaker, Inc., Walkersville, Md.) containing 1% HSA and PIXY 321 at 100 ng/ml (Complete Media). PIXY is a fusion protein containing the active domains of both IL-3 and GM-CSF. Depending on the number of cell:bead complexes obtained, the suspension was then placed in a gas- permeable culture bag (Baxter, Roundlake, Ill.) and incubated for 48 hours in a cell culture incubator set at 5% carbon dioxide and 37° C. The starting culture medium was 20–50 mls in volume. These containers were referred to as the primary culture containers.

Following a 48 hour culture release period the released cells were retrieved from the culture by removal of the magnetic beads using the MaxSep™ Cell Separator (Baxter Healthcare, Corp., Irvine, Calif.) (Day 9 of culture). The released cells were then transferred into a secondary culture container and cultured as described in Example 3.

At day 5, the cultures were analyzed for cell number and cell viability using a hemacytometer and trypan blue viability staining. The cell concentration was then readjusted to $1 \times 10^5$ cells/ml with Complete Media and cultured for an additional 5 days. Flow cytometry, colony assays and morphology evaluations were performed as described in Examples 5–7.

Table 10 below summarizes the results of 5 experiments for cell proliferation at day 5 and 10 in which the viable proliferation index (P.I.) was calculated by dividing the total number of cells at day 5 or 10 by the total number of cells at day 0 and then multiplying by the % viable.

TABLE 10

| VIABLE PROLIFERATION INDEX AT DAY 5 AND DAY 10 OF CULTURE | | |
|---|---|---|
| CULTURE I.D. | DAY 5 | DAY 10 |
| A.E (11/22/93) | 2 | 7 |
| L.D. (11/22/93) | 2 | 14 |
| C1514 (12/11/93) | 4 | 14 |
| C1515 (12/11/93) | 8 | 40 |
| V.T. (12/31/93) | 2 | 25 |
| MEAN ± S.D. (n = 5) | 4 ± 2 | 20 ± 13 |

The increases in cell number, total CFU, clusters, CFU-GM, CD15$^+$ cells, and early granulocytes at day 10 of culture were also determined. The increases in total CFU, clusters, and CFU-GM were calculated from the change in the numbers present at day 0 to the final numbers at day 10 relative to the P.I. (Table 11). The increase in CD15$^+$ cells and early granulocytes at day 10 of culture takes into account that 80±17% (mean purity) of the cells were CD34$^+$ and defined as blasts at day 0.

These results show that the serum-free X-VIVO 10 media supplemented with only 1% HSA and the IL-3 and GM-CSF growth factors were able to support the proliferation of neutrophil progenitors and maintain good cell viability (89±3%) in a 10-day liquid culture (Table 11). As stated above the cells used in these experiments had a mean CD34 purity of 80±20% when selected with the magnetic cell separator (Table 12). The percentage of CD15$^+$ cells, CFUs and cell morphology are presented in Tables 12–14. The distribution of early granulocytes as observed by cell morphology were not significantly different as shown in Table 14. However, the total number of early granulocytes was significantly different when the number of cells counted per 100 cells was multiplied by the P.I.

TABLE 11

| | PROLIFERATION INDEX AT DAY 5 AND 10, PERCENT OF VIABLE CELLS AT DAY 0, 5, AND 10 | | | | | | |
|---|---|---|---|---|---|---|---|
| | DAY 0 | | DAY 5 | | | DAY 10 | |
| CULTURE | % VIABLE | P.I. | % VIABLE | VIABLE P.I. | P.I. | % VIABLE | VIABLE P.I. |
| MEAN (n = 5) | 90 | 4.0 | 89 | 3.6 | 22.9 | 89 | 20.0 |
| STDEV | 8 | 2.6 | 4 | 2A | 15.5 | 3 | 13.0 |

TABLE 12

CD34 PURITY AT DAY 0, CD15 AND CD11B
PHENOTYPE AT DAY 10 OF CULTURE

| CULTURE | % CD34+ DAY 0 | % CD15− % CD11b− | % CD15− % CD11b+ | % CD15+ % CD11b+ | % CD15+ % CD11b− | TOTAL % CD15+ |
|---|---|---|---|---|---|---|
| MEAN (n = 5) | 80 | 36.05 | 22.38 | 15.52 | 26.05 | 41.57 |
| STDEV | 21 | 8.11 | 6.39 | 1.78 | 6.32 | 6.23 |

TABLE 13

COLONY FORMING UNITS (CFU) PER 10,000 CELLS
AT DAY 0 AND DAY 100 OF CULTURE

| | DAY | CFU-GM | CFU-Mac | BFUE | CFU-MIX | TOTAL CFU | CLUSTERS |
|---|---|---|---|---|---|---|---|
| CULTURE MEAN (n = 5) | 0 10 | 652 51 | 122 3 | 318 108 | 82 3 | 1174 165 | 41 28 |
| CULTURE STDEV | 0 10 | 334 19 | 124 3 | 337 75 | 105 4 | 806 5 | 46 23 |

TABLE 14

CELL MORPHOLOGY PER 100 CELLS AT DAY 10 OF CULTURE

| | | EARLY GRANULOCYTES | | | |
|---|---|---|---|---|---|
| CULTURE | BLASTS | PROMYELOCYTES | MYELOCYTES | METAMYELOCYTES | MONOCYTES |
| MEAN (n = 5) | 20 | 38 | 26 | 1 | 14 |
| STDEV | 15 | 15 | 15 | 1 | 5 |

In a separate experiment, the growth and differentiation of CD34+ cells into megakaryocytes in X-VIVO 10 supplemented with various combinations of IL-3, SCF and IL-6 was assessed. Briefly, CD34+ cells were cultured in X-VIVO 10 media containing 1% HSA, 300 U/ml IL-3 and 20 ng/ml SCF with or without the addition of 40 ng/ml IL-6. At day 11 of culture, cell counts were performed and analyzed for the percentage of CD4a+ cells by immunocytochemistry. The results from 5 independent experiments are shown below in Tables 15–17. The data indicate that 1) CD41a+ cells can be generated in this serum-free media under these conditions, and 2) that there was no significant difference seen on the proliferation index of CD34+ cells, percentage of CD41a+ cells and the total number of megakaryocytes in the presence or absence of IL-6. Thus, the human hematopoietic cell compositions described herein can be cultured in serum-free media containing, for example, just IL-3 and SCF.

TABLE 15

PROLIFERATION OF DAY 12 CULTURED CD34+ CELLS

| SAMPLE | NO IL6 | R & D IL6 40 ng/ml |
|---|---|---|
| MEAN | 31.00 | 35.10 |
| S.D. | 13.30 | 15.50 |

TABLE 16

TWO PERCENT CD41a POSITIVE CELLS IN DAY 12 CULTURED CD34+ CELLS

| SAMPLE | NO IL6 | R & D IL6 40 ng/ml |
|---|---|---|
| MEAN | 27.0 | 21.6 |
| S.D. | 21.20 | 10.50 |

TABLE 17

TOTAL NUMBER OF CD41a+ CELLS IN DAY 12 CULTURED CD34+ CELLS × $10^6$

| SAMPLE | NO IL6 | R & D IL6 40 ng/ml |
|---|---|---|
| MEAN | 6.25 | 5.90 |
| S.D. | 3.68 | 1.63 |

EXAMPLE 11

COMPARISONS OF SERUM-FREE SUSPENSIONS OF HUMAN HEMATOPOIETIC CELLS

This example compares the proliferation of human hematopoietic stem/progenitor cells in various serum-free media and characterizes the precursor cells produced from the different cultures.

The isolation and culture of $CD34^{30}$ hematopoietic cells from peripheral blood (PB) was performed by methods similar to those described in Example 9. Apheresis products from five patients who received G-CSF during recovery from cyclophosphamide chemotherapy were used for the comparison of proliferation and precursor production. Briefly, following isolation of CD34+ cells, cultures were seeded on day 0 with the selected cells at a density of $1-5 \times 10^4$ cells/ml in either X-vivo 10, X-vivo 15 or X-vivo 20 (BioWhittaker). The media was supplemented with 300 U/ml IL-3, 40ng/ml IL-6 and 20 ng/ml SCF and the cultures were incubated at 37° C., 5% $CO_2$, 5% $O_2$ and high humidity for 8–12 days. The percentage of CD34+ cells was determined as described in Example 9. Similarly, procedures for flow cytometry, cell morphology determination and immunochemistry were performed as described in Example 9.

To determine whether either of the three medias resulted in differential isolation of CD34+ cells, the percentage of CD34+ cells was determined by flow cytometry at day 0 of culture. The results showed no difference in purity with CD34+ cells comprising between 92% and 99% of the cultures in each of the medias. Similarly, no difference was seen in the cell viability or morphology following release in either the X-vivo 10, X-vivo 15 or X-vivo 20 medias.

Expansion of the CD34$^+$ cells was determined at the end of the culture period by calculation of the proliferation index (total number of cells at day 10/number of cells at day 0). Results determined from all five cultures showed no significant difference between the serum-free medias with the mean proliferation indexes being 95.8±22.0, 112.0±7.4 and 170.2±39.5 for X-vivo 10, 15 and 20, respectively. However, in three of the five cultures, the proliferation index of cells grown in X-vivo 20 was significantly higher then those observed using the either of the other two medias (p=0.047, paired t test). These results indicate that all three serum-free medias support the growth of human hematopoietic cells. In cultures that are highly proliferatory, X-vivo 20 can out perform either x-vivo 10 or 15 for cell expansion.

The percentage of early neutrophil precursors (CD15$^+$/CD11b$^-$) was as also determined in each of the serum-free medias. The results obtained again showed no significant difference in any of the medias. Specifically, the mean percentage of neutrophil precursors for each of the five cultures was 20.76±5.98, 17.20±6.63 and 17.63±6.20 for X-vivo 10, X-vivo 15 and X-vivo 20, respectively. Conversely, the percentage of more mature neutrophils was less then 5% in all cultures in the 10 day time period.

Megakaryocyte percentages was also determined in the above cultures at the end of the culture period. The results showed that X-vivo 10 had a significantly higher percentage of CD41a$^+$ cells as determined by flow cytometry compared to X-vivo 15 and 20 (p=0.0247 and p=0.0211 paired t test, respectively). When assessed by immunochemistry, the data paralleled the results obtained by flow cytometry. The results are shown below in Table 18.

TABLE 18

PERCENTAGE OF MEGAKARYOCYTES (CD41a$^+$) FROM CD34$^+$ CELLS CULTURED IN SERUM-FREE MEDIA

| SAMPLE | X-VIVO 10 | | X-VIVO 15 | | X-VIVO 20 | |
|---|---|---|---|---|---|---|
| | FACS | ICC | FACS | ICC | FACS | ICC |
| MEAN | 9.39 | 10.25 | 6.00 | 6.60 | 6.37 | 8.50 |
| ± S.D. | 3.75 | 1.70 | 3.47 | 3.43 | 3.43 | 5.19 |

FACS: percentage CD41a$^+$ cells determined by flow cytometry
ICC: percentage CD41a$^+$ cells determined by immunochemistry The total number of neutrophil precursors and megakaryocyte cells expanded in each of the three serum-free medias was also assessed. The cell expansion for each lineage was determined by multiplying the initial number of CD34$^+$ cells ($10^6$) by the proliferation index at day 10 and by the percentage of cells within the particular lineage. For both lineages, the results indicate that there was no significant difference between each of the medias. For example, the fold expansion of neutrophil precursors was 20.9±4.7, 17.20±2.98 and 17.63±2.77 in X-vivo 10, 15 and 20, respectively. Fold expansion for megakaryocytes was determined to be 9.77±3.1, 6.6±1.9 and 12.2±4.7 in X-vivo 10, 15 and 20, respectively.

EXAMPLE 12

Large scale closed culture for the production of neutrophil and megakaryocyte precursors CD34+ cells were isolated from peripheral blood using the Isolex®300 Magnetic Cell Separator (Baxter) from 8 apheresis products. Six of the apheresis products were from healthy volunteers in whom hematopoeitic cells had been mobilized into the peripheral blood by treatment with G-CSF. Two of the apheresis products were from cancer patients whose hematopoietic cells had been mobilized into peripheral blood by treatment with chemotherapy (Cy/VP16) and a cytokine (G-CSF). An average of $1.1 \times 10^8$ CD34+ cells (75±19% recovery, n=8) were collected and cultured at $10^5$ cells/ml in culture bags containing 1L of X-VIVO®10 medium supplemented with 1% HSA and 100 ng/ml of the IL-3/GM-CSF fusion protein, PIXY®321. After 7 days the cultures were fed and readjusted to $10^5$ cells/ml. Final culture volumes at day 12 averaged 3L (range 1–6L) with an average fold increase in cell number of 41±16X (n=8). Using the CS3000®, the cultures were washed with Plasmalyte®A (Baxter), and concentrated in a final volume of 200 ml with a 91±14% recovery and an 86±7% viability.

Results are shown in Table 19 below:

TABLE 19

| | Characterization of Neutrophil/Monocytes | | | | | | |
|---|---|---|---|---|---|---|---|
| | NV495C | NV279B | NV236A | NV86B | NV638 | PT1 | PT2 |
| PHENOTYPE | | | | | | | |
| % CD15– 11b– | 44% | 44% | 37% | 27% | 0% | 3% | 30% |
| % CD15+ 11b– | 14% | 20% | 13% | 24% | 60% | 45% | 26% |
| % CD15+ 11b+ | 18% | 16% | 21% | 15% | 40% | 44% | 17% |
| % CD15– 11b+ | 24% | 20% | 28% | 34% | 0% | 7% | 27% |
| MORPHOLOGY | | | | | | | |
| % Blasts | 25% | 26% | 17% | 8% | 38% | 4% | 10% |
| % Neut. Prec. | 61% | 57% | 68% | 74% | 55% | 90% | 82% |
| % Monocyte | 8% | 17% | 12% | 10% | 7% | 6% | 8% |

Results from phenotypic assays conducted by flow cytometry on the basis of labeling with anti-CD15 and anti-CD11b antibodies are depicted in Table 19 (phenotype). Morphological analysis (Wright-Giemsa staining) of the four phenotypic subgroups in Table 19 demonstrated that:

CD15−11b− were blasts

CD15+11b− were promyelocytes and myelocytes

CD15+11b+ were predominately myelocytes and metamyelocytes, and

CD15−11b+ were monocytes.

The morphology of CD15+CD11b+ cells grown in serum-free culture, as shown here, contrasted sharply with the morphology of cells of the same phenotype grown in serum-containing cultures. It was previously reported that CD15+/CD11b+ cells which had been either isolated from peripheral blood or grown in serum-containing medium were predominately mature segmented and band form neutrophils. However, in the present cultures grown in serum-free conditions, the cells which simultaneously express the CD15 and CD11b antigens were found to be predominately myelocytes and metamyelocytes, with less than 5% mature segmented and band forms.

Direct morphological analysis of Wright-Giemsa-stained cultures (Table 19, Morphology) showed that the cell product contained 71±11% neutrophil precursors (defined as promyelocytes, myelocytes, and metamyelocytes).

A relatively high percentage of CD41a+ megakaryocyte precursors (9.7%) was also observed in these cultures.

Two of the cultures were analyzed for content of CD34+ cells. At day 0 there were $9.77\pm1.0\times10^7$ total CD34+ cells in a culture of $1.3\pm0.48\times10^8$ total cells; at day 12 there were $1.2\pm1.2\times10^8$ total CD34+ cells in a culture of $4.6\pm2.9\times10^9$ total cells.

An additional fourteen CD34+ cell preparations from stage III/IV breast cancer patients were studied for presence of tumor cells. Tumor cell detection was done by immunocytochemistry to detect the expression of cytokeratin antigens and surface antigens found on breast cancer cells. Five pre-culture samples contained detectable tumor cells in starting MNCs. No tumor cells were found in post-culture samples. This discovery suggests that either CD34+ selection effectively purges the MNC preparation of tumor cells, or, if any tumor cells remain among the CD34+ selected cells, expansion of tumor cells is not supported by the culture conditions.

EXAMPLE 13

Treatment for cytopenia

Four patients with metastatic breast cancer underwent peripheral blood progenitor cell (PBPC) mobilization with cyclophosphamide (Cy) (4gm/m$^2$), VP-16 (Etoposide®) (1 gm/m$^2$), and G-CSF (Neupogen®)(10µg/kg/d). Then patients underwent four or five apheresis procedures. Three or four of the apheresis products were cryopreserved. CD34+ cells were selected from the second apheresis product and cultured as described in Example 12 above.

Characterization of day 12 cutures is shown in Table 20 below:

TABLE 20

| Pt ID | CD34+ Cell Purity (%) | Total Cells Day 0 ×10*7 | Total Cells Day 12 ×10*7 | Fold Expand | % Viable in Final Product | % CD15+ in Final Product | Cultured Cells Infused × 10*6 | Morph % Gran* |
|---|---|---|---|---|---|---|---|---|
| 3000 | 98.2 | 3.68 | 118.2 | 59 | 83 | 26.7 | 29.8 | 72 |
| 3001 | 73.4 | 3.20 | ND | ND | ND | ND | ND | ND |
| 3002 | 98.0 | 9.40 | 169 | 18 | 87 | 29.7 | 66.0 | 81 |
| 3003 | 64.0 | .92 | 7.5 | 8 | 86 | 48.1 | 1.4 | 81 |
| 3004 | 98.7 | 49.10 | 1200 | 24 | 92 | 332 | 498 | 83 |

*Granulocytes = Promyelocytes, Myetocytes, Metamyelocytes

All cultures contained more than 65% neutrophil precursors, as determined by morphological analysis on Wright-Giemsa-stained samples. As described above, neutrophil precursors are defined as promyelocytes, myelocytes, and metamyelocytes. The values in the column in Table 20 labeled "Morph % Gran" include less than 5% mature neutrophils (segmented and band forms), while the remainder were neutrophil precursors.

There was no evidence of tumor cell contamination of the cultures on immunocytochemical staining for cytokeratin.

Patients underwent high-dose chemotherapy (HDC) with Cy (6gm/m$^2$), carboplatin (800mg/m$^2$), and thiotepa (600mg/m$^2$). The protocol is shown in Table 21 below:

TABLE 21

Induction chemotherapy/PBSC mobilization

| Day | 1 | 2 | 3 | 4 | 5 | 6 | 7 | 8 | 9 | 10 | 11 | 12 | 13 | 14 | 15 | 16 | 17 | |
|---|---|---|---|---|---|---|---|---|---|---|---|---|---|---|---|---|---|---|
| cy | X | X | | | | | | | | | | * | * | * | * | | | 2 gm/m2, 12 hr × 2 |
| Vp16 | | X | | | | | | | | | | | | | | | | 1 gm/m2 over 8 hrs |
| G-CSF | | | X | X | X | X | X | X | X | X | X | X | X | | | | | X 10 ug/kg/d (stop ANC > 75 K/ul) |

\* Apheresis begins, Platelet > 20 K/ul, WBC > 1,000/ul

High dose chemotherapy and PBSC/Cultured PBPC rescue

| Day | −7 | −6 | −6 | −4 | −3 | −2 | −1 | 0 | 1 | 2 | 3 | 4 | 5 | 6 | 7 | 8 | 9 | 10 | 11 |
|---|---|---|---|---|---|---|---|---|---|---|---|---|---|---|---|---|---|---|---|
| CY(1.5 gm/m2 = 4) | X | X | X | X | | | | | | | | | | | | | | | |
| CY(1.5 gm/m2 = 4) | X | X | X | X | | | | | | | | | | | | | | | |
| CP(200 mg/m2 = 2) | X | X | X | X | | | | | | | | | | | | | | | |
| Thawed cells | | | | | | | | X | | | | | | | | | | | |
| Cultured cells | | | | | | | X | | | | | | | | | | | | |
| G-CSF(5 ug/kg/d) | | | | | | | | X | X | X | X | X | X | X | X | X | X | X | X |

On day 0 the cryopreserved cells were reinfused.

On day +1 the 12-day cultured cells were harvested and washed using the CS3000 ®Plus Cell Separator and suspended in approximately 200 mls of a reinfusion solution consisting of Plasma-Lyte®A (Baxter) supplemented with 1% Human Albumin (Baxter Hyland). The cells were kept at room temperature, and samples were evaluated for cell number recovery and percent viability by trypan blue or propidium iodide exclusion.

The washed and suspended 12-day cultured cells were then brought to the patient's room for infusion. The dose range for these cells was 7.5–1200×10$^7$ total cells in a volume of 150–200mls. The cells were given through a central line at an approximate rate of 20–50 ml/min. Vigorous fluid hydration was begun at a rate of 3 L/m$^2$/day 4 hours prior to the infusion and discontinued 24 hours after the completion of the cell infusion. The urine pH was maintained between 6.5 and 7.5 with NaHCO$_3$ infusion. Vital signs and toxicity observations were made and recorded for 24 hours following the administration of cells.

Administration of G-CSF (5µg/kg/d) was begun on Day 0 and continued until the patient reached an absolute neutrophil count (ANC) of 50,000/µl. The administration of G-CSF is believed to help promote the differentiation in vivo of infused neutrophil precursors towards mature neutrophils.

Results

There was no toxicity resulting from cell infusions, nor was there any interference with platelet recovery. All four patients promptly recovered their ANC and platelets. Their recovery time to ANC of 500/µl ranged from 7–10 days.

What is claimed is:

1. A method of treating a human patient having a reduced population of neutrophils, comprising the steps of:
   (a) preparing a serum-free, animal protein-free human cell suspensions, comprising at least 25% neutrophil precursors, said neutrophil precursors being selected from the group consisting of promyelocytes, myelocytes, and metamyelocytes, and
   (b) administering said cell suspension to the patient, wherein said suspension is administered in a therapeutically effective amount to increase the population of neutrophils in said patient.

2. The method of claim 1, further comprising the additional step of, after step (b), administering G-CSF to the patient.

3. The method of claim 1, wherein the cell suspension comprises at least 60% neutrophil precursors.

4. The method of claim 1 wherein the cell suspension further comprises about 3 to 25% monocytes, and less than about 0.01% mast cells.

5. The method of claim 1 wherein the cell suspension further comprises colony-forming units (CFU) and cluster-forming units (clFU).

6. The method of claim 5 wherein at least about 40% of the total CFU/clFU are granulocyte-macrophage colony forming units, and at least about 40% of the total CFU/clFU are granulocyte cluster forming units.

7. The method of claim 1 wherein the cell suspension is prepared by obtaining hematopoietic cells from peripheral blood, chord blood, or bone marrow, and culturing for 7 to 14 days in a serum-free, animal-protein free culture medium containing at least one hematopoietic growth factor.

8. The method of claim 1 wherein the cell suspension is prepared by obtaining hematopoietic cells from peripheral blood of the patient to be treated following peripheral blood progenitor cell mobilization.

9. The method of claim 1, wherein the serum-free, animal protein-free cell suspension is administered to the patient at a dosage of at least approximately 3×10$^5$ total cells.

10. The method of claim 1 wherein the cells are administered to the patient by intravenous infusion.

11. The method of claim 1 wherein the cell suspension is administered to the patient following the administration of high dose chemotherapy.

12. The method of claim 9, further comprising step (c), co-administering G-CSF daily to the patient until a neutrophil count of about 50,000/ml is obtained.

13. The method of claim 1 wherein the cell suspension is administered to the patient following the administration of myeloablative cancer treatment.

14. The method of claim 1 wherein the cell suspension is administered to the patient following the administration of chemotherapy.

* * * * *

UNITED STATES PATENT AND TRADEMARK OFFICE
CERTIFICATE OF CORRECTION

PATENT NO. : 5,846,529
DATED : Dec. 8, 1998
INVENTOR(S) : Smith et al.

It is certified that error appears in the above-identified patent and that said Letters Patent is hereby corrected as shown below:

In column 15, TABLE 2, B.M. Culture Medium Table, fifth column, line 3, please delete "0", and replace therefor with --9--.

In column 15, TABLE 2, MEAN Culture Medium Table, eighth column, line 2, please delete "0.0" and replace therefor with --0.9--.

In column 15, TABLE 2, MEAN Culture Medium Table, eighth column, line 6, please delete "14" and replace therefor with --1.4--.

In column 17, TABLE 4, ninth column, line 25, please delete "49" and replace therefor with --40--.

In column 20, TABLE 5, seventh column, line 17, please delete "93.4" and replace therefor with --90.4--.

In column 20, line 61, please delete "Coniditions" and replace therefor with --Conditions--.

In column 22, line 65, please delete "CM-CSF" and replace therefor with --GM-CSF--.

UNITED STATES PATENT AND TRADEMARK OFFICE
CERTIFICATE OF CORRECTION

PATENT NO. : 5,846,529
DATED : Dec. 8, 1998
INVENTOR(S) : Smith et al.

It is certified that error appears in the above-identified patent and that said Letters Patent is hereby corrected as shown below:

In column 25, line 40, please add a carriage return after "proliferation."

In column 28, TABLE 11, line 4, please delete "DAYS" and replace therefor with --DAY 5--.

In column 29, line 47, please delete "CD4a$^+$" and replace therefor with --CD41a$^+$--.

In column 30, line 44, please delete "CD34$^{30}$" and replace therefor with --CD34$^+$--.

In column 32, TABLE 19, line 13, fourth column, please delete "12%" and replace therefor with --13%--.

In column 34, TABLE 20, line 10, third column, please delete "49.10" and replace therefor with --49.70--.

In column 34, TABLE 20, line 10, seventh column, please delete "332" and replace therefor with --33.2--.

In column 35, TABLE 21, line 10, third column, please delete the second "-6" and replace therefor with ---5--.

UNITED STATES PATENT AND TRADEMARK OFFICE
CERTIFICATE OF CORRECTION

PATENT NO. : 5,846,529
DATED : Dec. 8, 1998
INVENTOR(S) : Smith et al.

It is certified that error appears in the above-identified patent and that said Letters Patent is hereby corrected as shown below:

In column 35, TABLE 21, line 12, first column, please delete "gm/m2 = 4)" and replace therefor with --gm/m2 x 4)--.

In column 35, TABLE 21, line 13, first column, please delete "CY(1.5 gm/m2 = 4)" and replace therefor with --TT(150 mg/m2 x 4)--.

In column 35, TABLE 21, line 14, first column, please delete "mg/m2 = 2)" and replace therefor with --mg/m2 x 4)--.

In column 35, line 49, please delete "Results" and replace therefor with --Results:--.

Signed and Sealed this

Seventeenth Day of April, 2001

Attest:

NICHOLAS P. GODICI

*Attesting Officer*   *Acting Director of the United States Patent and Trademark Office*